US009612364B2

(12) United States Patent
Mahadevan et al.

(10) Patent No.: US 9,612,364 B2
(45) Date of Patent: *Apr. 4, 2017

(54) MEDICAL DEVICES HAVING HOMOGENEOUS CHARGE DENSITY AND METHODS FOR MAKING SAME

(71) Applicant: Johnson & Johnson Vision Care, Inc., Jacksonville, FL (US)

(72) Inventors: Shivkumar Mahadevan, Orange Park, FL (US); Zohra Fadli, Jacksonville, FL (US); Charles Scales, St. Augustine, FL (US); Thomas Maggio, Jacksonville, FL (US); Kunisi Venkatasubban, Jacksonville, FL (US); Eric R. George, St. Augustine, FL (US); James D. Ford, Orange Park, FL (US); Carrie L. Davis, St. Augustine, FL (US); Leah Hansen, Jacksonville, FL (US); Scott L. Joslin, Ponte Vedra Beach, FL (US); Douglas G. Vanderlaan, Jacksonville, FL (US); Ranganath Raja, Jacksonville, FL (US); Sharmila Muthukrishnan, Chennai (IN); C. Surendran, The Nilgris (IN); R. Sridharan, Chennai (IN)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/657,217

(22) Filed: Mar. 13, 2015

(65) Prior Publication Data
US 2015/0185365 A1    Jul. 2, 2015

Related U.S. Application Data

(60) Division of application No. 13/829,592, filed on Mar. 14, 2013, now abandoned, which is a continuation-in-part of application No. 13/449,413, filed on Apr. 18, 2012, now Pat. No. 9,170,349.

(60) Provisional application No. 61/482,379, filed on May 4, 2011.

(51) Int. Cl.
| | |
|---|---|
| *G02B 1/04* | (2006.01) |
| *A61K 6/083* | (2006.01) |
| *A61K 47/34* | (2017.01) |
| *A61K 31/4535* | (2006.01) |
| *A61K 9/00* | (2006.01) |

(52) U.S. Cl.
CPC ............ *G02B 1/043* (2013.01); *A61K 9/0051* (2013.01); *A61K 31/4535* (2013.01); *A61K 47/34* (2013.01); *G02B 1/041* (2013.01)

(58) Field of Classification Search
CPC ................ G02B 1/041; C08L 33/14

USPC ............................................ 523/107; 528/25
See application file for complete search history.

(56) References Cited

U.S. PATENT DOCUMENTS

| | | |
|---|---|---|
| 3,408,429 A | 10/1968 | Wichterle |
| 3,660,545 A | 5/1972 | Wichterle |
| 3,808,178 A | 4/1974 | Gaylord |
| 4,018,853 A | 4/1977 | Le Boeuf et al. |
| 4,113,224 A | 9/1978 | Clark et al. |
| 4,120,570 A | 10/1978 | Gaylord |
| 4,136,250 A | 1/1979 | Mueller et al. |
| 4,139,513 A | 2/1979 | Tanaka et al. |
| 4,153,641 A | 5/1979 | Deichert et al. |
| 4,168,112 A | 9/1979 | Ellis et al. |
| 4,190,277 A | 2/1980 | England |
| 4,197,266 A | 4/1980 | Clark et al. |
| 4,287,175 A | 9/1981 | Katz |
| 4,321,261 A | 3/1982 | Ellis et al. |
| 4,436,730 A | 3/1984 | Ellis et al. |
| 4,495,313 A | 1/1985 | Larsen |
| 4,557,264 A | 12/1985 | Hinsch |
| 4,663,409 A | 5/1987 | Friends et al. |
| 4,680,336 A | 7/1987 | Larsen et al. |
| 4,740,533 A | 4/1988 | Su et al. |
| 4,889,664 A | 12/1989 | Kindt-Larsen et al. |
| 4,910,277 A | 3/1990 | Bambury et al. |
| 5,006,622 A | 4/1991 | Kunzler et al. |
| 5,034,461 A | 7/1991 | Lai et al. |
| 5,039,459 A | 8/1991 | Kindt-Larsen et al. |
| 5,070,215 A | 12/1991 | Bambury et al. |
| 5,177,165 A | 1/1993 | Valint, Jr. et al. |
| 5,219,965 A | 6/1993 | Valint, Jr. et al. |
| 5,244,981 A | 9/1993 | Seidner et al. |
| 5,256,751 A | 10/1993 | Vanderlaan |
| 5,260,000 A | 11/1993 | Nandu et al. |
| 5,311,223 A | 5/1994 | Vanderlaan |
| 5,314,960 A | 5/1994 | Spinelli et al. |
| 5,319,589 A | 6/1994 | Yamagata et al. |
| 5,321,108 A | 6/1994 | Kunzler et al. |
| 5,331,067 A | 7/1994 | Seidner et al. |

(Continued)

FOREIGN PATENT DOCUMENTS

| | | |
|---|---|---|
| CN | 10166334 A | 3/2010 |
| DE | 4143239 A1 | 7/1993 |

(Continued)

OTHER PUBLICATIONS

PCT International Preliminary Report on Patentability, dated Nov. 25, 2014, for PCT/US2013/040066.

(Continued)

*Primary Examiner* — Tae H Yoon
(74) *Attorney, Agent, or Firm* — Raef M. Shaltout

(57) ABSTRACT

The present invention relates to ionic silicone hydrogel polymers comprising at least one pharmaceutical or nutriceutical component and displaying improved lysozyme uptake, low contact angle and reduced water soluble polymeric ammonium salt uptake.

26 Claims, No Drawings

(56) References Cited

U.S. PATENT DOCUMENTS

| | | | |
|---|---|---|---|
| 5,352,714 A * | 10/1994 | Lai | A61L 27/18 523/107 |
| 5,371,147 A | 12/1994 | Spinelli et al. | |
| 5,385,996 A | 1/1995 | Rizzardo et al. | |
| 5,387,662 A | 2/1995 | Kunzler et al. | |
| 5,451,617 A | 9/1995 | Lai et al. | |
| 5,525,691 A | 6/1996 | Valint, Jr. et al. | |
| 5,539,016 A | 7/1996 | Kunzler et al. | |
| 5,700,559 A | 12/1997 | Sheu et al. | |
| 5,723,255 A | 3/1998 | Texter et al. | |
| 5,760,100 A | 6/1998 | Nicolson et al. | |
| 5,805,264 A | 9/1998 | Janssen et al. | |
| 5,874,511 A | 2/1999 | Rizzardo et al. | |
| 5,942,558 A | 8/1999 | Korb | |
| 5,944,853 A | 8/1999 | Molock et al. | |
| 5,962,548 A | 10/1999 | Vanderlaan et al. | |
| 5,998,498 A | 12/1999 | Vanderlaan et al. | |
| 6,020,445 A | 2/2000 | Vanderlaan et al. | |
| 6,087,412 A | 7/2000 | Chabrecek et al. | |
| 6,087,415 A | 7/2000 | Vanderlaan et al. | |
| 6,099,852 A | 8/2000 | Jen | |
| 6,277,365 B1 | 8/2001 | Ellis et al. | |
| 6,367,929 B1 | 4/2002 | Maiden et al. | |
| 6,428,839 B1 | 8/2002 | Kunzler et al. | |
| 6,433,061 B1 | 8/2002 | Marchant et al. | |
| 6,458,142 B1 | 10/2002 | Faller et al. | |
| 6,637,929 B2 | 10/2003 | Baron | |
| 6,794,486 B2 | 9/2004 | Adam et al. | |
| 6,822,016 B2 | 11/2004 | McCabe et al. | |
| 6,858,310 B2 | 2/2005 | McGee et al. | |
| 6,867,245 B2 | 3/2005 | Iwata et al. | |
| 7,109,276 B2 | 9/2006 | Wilczewska et al. | |
| 7,553,880 B2 | 6/2009 | Nicolson et al. | |
| 7,566,746 B2 | 7/2009 | Winterton et al. | |
| 7,592,341 B2 | 9/2009 | Tomich et al. | |
| 7,705,067 B2 | 4/2010 | Winterton et al. | |
| 7,807,755 B2 | 10/2010 | Farnham et al. | |
| 7,816,454 B2 | 10/2010 | Higashira et al. | |
| 7,816,464 B2 | 10/2010 | Farcet | |
| 8,158,695 B2 | 4/2012 | Vanderlaan et al. | |
| 8,273,366 B2 | 9/2012 | Chauhan et al. | |
| 8,337,551 B2 | 12/2012 | Linhardt et al. | |
| 9,170,349 B2 * | 10/2015 | Mahadevan | G02B 1/041 |
| 2002/0016383 A1 | 2/2002 | Iwata et al. | |
| 2003/0125498 A1 | 7/2003 | McCabe et al. | |
| 2003/0162862 A1 | 8/2003 | McCabe et al. | |
| 2004/0116310 A1 | 6/2004 | Kunzler et al. | |
| 2004/0208983 A1 | 10/2004 | Hill et al. | |
| 2005/0031793 A1 | 2/2005 | Moeller et al. | |
| 2005/0085561 A1 | 4/2005 | Phelan et al. | |
| 2005/0176911 A1 | 8/2005 | Zanini et al. | |
| 2005/0192610 A1 | 9/2005 | Houser et al. | |
| 2005/0208102 A1 * | 9/2005 | Schultz | A61K 9/0048 424/427 |
| 2006/0063852 A1 | 3/2006 | Iwata et al. | |
| 2006/0072069 A1 | 4/2006 | Laredo et al. | |
| 2006/0187410 A1 | 8/2006 | Sato et al. | |
| 2007/0116740 A1 | 5/2007 | Valint, Jr. et al. | |
| 2007/0122540 A1 | 5/2007 | Salamone et al. | |
| 2007/0155851 A1 | 7/2007 | Alli et al. | |
| 2007/0232783 A1 | 10/2007 | Moad et al. | |
| 2008/0045612 A1 | 2/2008 | Rathore et al. | |
| 2008/0143957 A1 | 6/2008 | Linhardt et al. | |
| 2008/0151236 A1 | 6/2008 | Prince et al. | |
| 2008/0174035 A1 | 7/2008 | Winterton | |
| 2008/0273168 A1 | 11/2008 | Rathore et al. | |
| 2008/0307751 A1 | 12/2008 | Newman et al. | |
| 2008/0314767 A1 | 12/2008 | Lai et al. | |
| 2009/0029043 A1 | 1/2009 | Rong et al. | |
| 2009/0108479 A1 | 4/2009 | Lai et al. | |
| 2009/0141236 A1 | 6/2009 | Chen et al. | |
| 2009/0142292 A1 | 6/2009 | Blackwell et al. | |
| 2009/0168012 A1 | 7/2009 | Linhardt et al. | |
| 2009/0169716 A1 | 7/2009 | Linhardt et al. | |
| 2009/0171049 A1 | 7/2009 | Linhardt et al. | |
| 2009/0171459 A1 | 7/2009 | Linhardt et al. |
| 2009/0173044 A1 | 7/2009 | Linhardt et al. |
| 2009/0176676 A1 | 7/2009 | Hilvert et al. |
| 2009/0186229 A1 | 7/2009 | Muller et al. |
| 2010/0048847 A1 | 2/2010 | Broad |
| 2010/0069522 A1 | 3/2010 | Linhardt et al. |
| 2010/0099829 A1 | 4/2010 | Parakka |
| 2010/0137548 A1 | 6/2010 | Moad et al. |
| 2010/0140114 A1 | 6/2010 | Pruitt et al. |
| 2010/0162661 A1 | 7/2010 | Vanderbilt et al. |
| 2010/0168852 A1 | 7/2010 | Vanderbilt et al. |
| 2010/0168855 A1 | 7/2010 | McGee et al. |
| 2010/0249356 A1 | 9/2010 | Rathore |
| 2010/0296049 A1 | 11/2010 | Justynska et al. |
| 2010/0298446 A1 | 11/2010 | Chang et al. |
| 2010/0315588 A1 | 12/2010 | Nunez et al. |
| 2010/0317809 A1 | 12/2010 | Linhardt et al. |
| 2010/0317816 A1 | 12/2010 | Linhardt et al. |
| 2010/0317817 A1 | 12/2010 | Linhardt et al. |
| 2010/0318185 A1 | 12/2010 | Nunez et al. |
| 2011/0102736 A1 | 5/2011 | Wu et al. |
| 2011/0112267 A1 | 5/2011 | Jakubowski et al. |
| 2011/0189291 A1 | 8/2011 | Yang et al. |
| 2011/0230589 A1 | 9/2011 | Maggio et al. |
| 2011/0237766 A1 | 9/2011 | Maggio et al. |
| 2011/0275734 A1 | 11/2011 | Scales et al. |
| 2011/0293522 A1 | 12/2011 | Wang et al. |
| 2012/0026457 A1 | 2/2012 | Qiu et al. |
| 2012/0109613 A1 | 5/2012 | Boyden et al. |
| 2013/0203812 A1 | 8/2013 | Raja et al. |
| 2013/0217620 A1 | 8/2013 | Alli et al. |

FOREIGN PATENT DOCUMENTS

| | | |
|---|---|---|
| DE | 4337492 C2 | 6/1999 |
| EP | 0080539 B1 | 6/1983 |
| EP | 1803754 A2 | 7/2007 |
| JP | 10512000 | 11/1998 |
| JP | 2009520219 A | 5/2009 |
| JP | 2009175543 A | 8/2009 |
| JP | 2010508902 A | 3/2010 |
| JP | 2011510350 A | 3/2011 |
| JP | 2011518347 A | 6/2011 |
| JP | 2012504182 A | 2/2012 |
| JP | 2012508809 A | 4/2012 |
| JP | 2012522111 A | 9/2012 |
| RU | 2334770 C1 | 9/2008 |
| RU | 2008131301 | 2/2010 |
| TW | 201026752 | 7/2010 |
| WO | 9631792 A1 | 10/1996 |
| WO | 9729788 A1 | 8/1997 |
| WO | 0171392 A1 | 9/2001 |
| WO | 03022321 A2 | 3/2003 |
| WO | 03022322 A2 | 3/2003 |
| WO | 2004040337 A1 | 5/2004 |
| WO | 2004056909 A1 | 7/2004 |
| WO | 2007070653 A2 | 6/2007 |
| WO | 2008061992 A2 | 5/2008 |
| WO | 2008112874 A1 | 9/2008 |
| WO | 2008124093 A1 | 10/2008 |
| WO | 2009085754 A1 | 7/2009 |
| WO | 2009085755 A1 | 7/2009 |
| WO | 2009085759 A1 | 7/2009 |
| WO | 2009089207 A1 | 7/2009 |
| WO | 2009117374 A1 | 9/2009 |
| WO | 2010039653 A1 | 4/2010 |
| WO | 2010056686 A1 | 5/2010 |
| WO | 2010117588 A1 | 10/2010 |
| WO | 2011071791 A | 6/2011 |
| WO | 2011140318 A | 11/2011 |

OTHER PUBLICATIONS

Babmann-Schnitzler et al, Sorption properties of hydrophobically modified poly(acrylic acids) as natural organic matter model substances to pyrene, Colloids and Surfaces A: Physiocochem. Eng. Aspects 260 (2005) 119-128.

(56) References Cited

OTHER PUBLICATIONS

Bannister, et al, "Development of Branching in Living Radical Copolymerization of Vinyl and Divinyl Monomers", Macromolecules 2006, vol. 39, pp. 7483-7492.
Burchard, "Particle Scattering Factors of Some Branched Polymers", Macromolecules 1977, vol. 10, No. 5, pp. 919-927.
Burchard, "Solution Properties of Branched Macromolecules", Advances in Polymer Science, 1999, vol. 143, pp. 113-194.
Burchard, et al, "Information on Polydispersity and Branching from Combined Quasi-Elastic and Integrated Scattering", Macromolecules 1980, vol. 13, pp. 1265-1272.
Crivello, et al, Photoinitiators for Free Radical Cationic & Anionic Photopolymerisation, 2nd Edition, vol. III, pp. 275-298, John Wiley and Sons, New York, 1998.
Encyclopedia of Polymer Science and Engineering, N-Vinyl Amide Polymers, Second edition, vol. 17, pp. 198-257, John Wiley & Sons Inc. and reported in K-values, 1989.
Gao et al "Synthesis of funcional polymers with controlled architecture by CRP of monomers in the presence of cross-linkers: From stars to gels", Progress in Polymer Science 2009, vol. 34, pp. 317-350.
Huan et al: "Synthesis and Properties of Polydimethylsiloxane-Containing Block Copolymers via Living Radical Polymerization", Journal of Polymer Science: Part A: Polymer Chemistry, vol. 39, 2001, pp. 1833-1842.
ISO 18369-4:2006: Ophthalmic optics—Contact lenses—Part 4: Physicochemical properties of contact lens materials.
ISO 9913-1: 1996(E).
Karunakaran et al, Synthesis. Characterization, and Crosslinking of Methacrylate-Telechelic PDMAAm-b-PDMS-b-PDMAAm Copolymers, Journal of Polymer Science: Part A: Polymer Chemistry, vol. 45, 4284-4290 (2007), Wiley Periodicals, Inc.
Lowe et al: "Reversible addition-fragmentation chain transfer (RAFT) radical polymerization and the synthesis of water-soluble (co)polymers under homogeneous conditions in organic and aqueous media", Prod. Polym. Sci. 32 (2007) 283-351.
McDowall et al: "Synthesis of Seven-Arm Poly(vinyl pyrrolidone) Star Polymers with Lysozyme Core Prepared by MADIX/RAFT Polymerization", Macromolecular Rapid Communication, vol. 29, 2008, pp. 1666-1671.
Mosmann, Rapid Calorimetric Assay for Cellular Growth and Survival: Application to Proliferation and Cytotoxicity Assays, Journal of Immunological Methods, 65 (1983) 55-63.
Pavlovic et al: "Synthesis and characterization of hydrophilic silicone copolymers and macromonomers for opthalmic application", Database accession No. 2008:955522; & Abstracts of Papers, 236th ACS National Meeting, philadelphia, PA, US, Aug. 17-21, 2008, POLY-113 Publisher: American Chemical Society, Washington, DC 2008.
PCT International Preliminary Report on Patentability, dated Nov. 5, 2013, for PCT Int'l Appln. No. PCT/US2012/035722.
PCT International Preliminary Report on Patentability, dated Nov. 25, 2014, for PCT Int'l Appln. No. PCT/US2013/042628.
PCT International Preliminary Report on Patenatability, dated Nov. 25, 2014, for PCT Int'l Appln. No. PCT/US2013/042644.
PCT International Preliminary Report on Patentability, dated Nov. 25, 2014, for PCT Int'l Appln. No. PCT/US2013/042658.
PCT International Preliminary Report on Patentability, dated Nov. 15, 2012, for PCT Int'l Appln. No. PCT/US2011/035324.
PCT International Search Report, dated Mar. 6, 2014, for PCT Int'l Appln. No. PCT/US2013/040066.
PCT International Search Report, dated Feb. 26, 2014, for PCT Int'l Appln. No. PCT/US2013/042628.
PCT International Search Report, dated May 27, 2014, for PCT Int'l Appln. No. PCT/US2013/042658.
PCT International Search Report, dated Aug. 11, 2011, for PCT Int'l Appln. No. PCT/US2011/035324.
PCT International Search Report, dated Jul. 11, 2012, for PCT Int'l Appln. No. PCT/US2012/035722.
PCT International Search Report, dated Oct. 29, 2013, for PCT Int'l Appln. No. PCT/US2013/042644.
Shedge et al, Hydrophobically Modified Poly(acrylic acid) Using 3-Pentadecycicyclohexylarnine: Synthesis and Rheology, Macromolecular Chemistry and Physics 2005, 206, 464-472.
Sugiyama, et al, "Evaluation of biocompatibility of the surface of polyethylene films modified with various water soluble polymers using Ar plasma-post polymerization technique", Macromolecular Materials and Engineering, (2000), 282, 5-12.
Vo, et al, "RAFT Synthesis of Branched Aacrylic Copolymers", Macromolecules 2007, Vol, 40, pp. 7119-7125.
Vogt, et al, "Tuning the Temperature Response of Branched Poly(N-isopropylacrylamide) Prepared by RAFT Polymerization", Macromolecules 2008, vol. 41, pp. 7368-7373.
Wooley, et al, A 'Branched-Monomer Approach' for the Rapid Synthesis of Dendimers**, Angew. Chem, Int. Ed. Engl. 1994, vol. 33, No. 1, pp. 82-85.

* cited by examiner

MEDICAL DEVICES HAVING HOMOGENEOUS CHARGE DENSITY AND METHODS FOR MAKING SAME

RELATED APPLICATIONS

This application is a division of U.S. patent application Ser. No. 13/829,592, filed Mar. 14, 2013, now abandoned, which is a continuation-in-part of U.S. patent application Ser. No. 13/449,413, filed on Apr. 18, 2012, now U.S. Pat. No. 9,170,349, which claims the benefit of U.S. Patent Provisional Application Ser. No. 61/482,379, filed May 4, 2011, entitled MEDICAL DEVICES HAVING HOMOGENEOUS CHARGE DENSITY AND METHODS FOR MAKING SAME, the contents of which are incorporated by reference.

FIELD OF THE INVENTION

The present invention relates to ionic silicone hydrogels, and ophthalmic devices formed therefrom, which display desirable tear and polycationic ophthalmic solution component uptake profiles and desirable drug uptake.

BACKGROUND OF THE INVENTION

It is well known that contact lenses can be used to improve vision. Various contact lenses have been commercially produced for many years. Hydrogel contact lenses are very popular today. These lenses are formed from hydrophilic polymers and copolymers containing repeating units from hydroxyethylmethylacrylate (HEMA). Of these contact lenses formed from copolymers of HEMA and methacrylic acid, are among the most comfortable, and have the lowest rate of adverse events. Contact lenses formed from copolymers of HEMA and MAA, such ACUVUE contact lenses, display substantial amounts of lysozyme uptake (greater than 500 µg) and retain a majority of the uptaken proteins in their native state. However, hydrogel contact lenses generally have oxygen permeabilities that are less than about 30.

Contact lenses made from silicone hydrogels have been disclosed. These silicone hydrogel lenses have oxygen permeabilities greater than about 60, and many provide reduced levels of hypoxia compared to conventional hydrogel contact lenses. Unfortunately, attempts to add anionic components to silicone hydrogels in the past have produced contact lenses which are not hydrolytically stable and display moduli which increase when exposed to water and heat. Also, while adding ionicity to silicone hydrogels has increased lysozyme uptake, it has also often increased uptake of positively charged components from contact lens multipurpose solutions. One such component is PQ1, a polyquaternium disinfecting compound. Also, many silicone hydrogels have higher than desired contact angles.

SUMMARY OF THE INVENTION

The present invention relates to anionic, silicone hydrogel contact lens comprising in or on said silicone hydrogel at least one statistical copolymer comprising units derived from at least 10 weight % of at least one non-ionic hydrophilic monomer and at least one anionic monomer and wherein said contact lens comprises at least one pharmaceutical or nutraceutical component and has a contact angle of about 70° or less, at least about 50 µg/lens lysozyme uptake, and less than about 10% uptake of at least one polycationic component when contacted with 3 mL of an ophthalmic solution comprising said 0.001 wt % polycationic component, 0.56% citrate dihydrate and 0.021% citric acid monohydrate (wt/wt).

In another embodiment the present invention relates to an anionic, silicone hydrogel contact lens comprising in or on said silicone hydrogel at least one statistical copolymer comprising units derived from at least 10 weight % of at least one non-ionic hydrophilic monomer and at least one anionic monomer and wherein said contact lens has a contact angle of about 70° or less, at least about 50 µg/lens lysozyme uptake, and less than about 10% uptake of at least one polycationic component when contacted with 3 mL of an ophthalmic solution comprising said 0.001 wt % polycationic component, 0.56% citrate dihydrate and 0.021% citric acid monohydrate (wt/wt)

In another embodiment the present invention relates to a silicone hydrogel formed from a reactive mixture comprising major polymerizable components comprising at least one reactive silicone-containing component, at least one reactive ionic monomer, optional reactive hydrophilic components and crosslinker; and minor polymerizable components selected from the group consisting of visibility tint and dyes, UV absorbers, photochromic compounds, pharmaceutical compounds, nutriceutical compounds, and mixtures thereof;

wherein said major polymerizable components comprise a single reactive functionality.

In another embodiment, the silicone hydrogels of the present invention comprise at least one statistical copolymer comprising units derived from at least one anionic monomer and at least 10 weight % of at least one non-ionic hydrophilic monomer.

DETAILED DESCRIPTION

The present invention relates to control of the spatial density and concentration of anionic charges in silicone hydrogel materials and articles made therefrom. It has been found that ionic silicone hydrogel polymers and articles made therefrom may be made having desirably increased tear component uptake (including lysozyme) and low or no uptake of polycationic components from cleaning and care solutions. The silicone hydrogels and articles made therefrom may be made from ionic statistical copolymers or may have associated therewith, at least one non-crosslinked (soluble), ionic statistical copolymer. In this embodiment the ionic statistical copolymer associates with the lens either through entanglement, association or a combination thereof. For example the contact lens may comprise NVP or PVP as a component in the lens body. In this embodiment, the anionic statistical copolymer forms a persistent association with the lactam moiety of the pyrrolidone. Alternatively the anionic statistical copolymer may comprise a hydrophobic block on at least one terminus. The hydrophobic block of the anionic statistical copolymer associates with the silicone in the silicone hydrogel contact lens.

As used herein, a "biomedical device" is any article that is designed to be used while either in or on mammalian tissues or fluid. Examples of these devices include but are not limited to catheters, implants, stents, and ophthalmic devices such as intraocular lenses, inlay lenses and contact lenses.

As used herein an "ophthalmic device" is any device which resides in or on the eye or any part of the eye, including the cornea, eyelids and ocular glands. These devices can provide optical correction, cosmetic enhancement, vision enhancement, therapeutic benefit (for example as bandages) or delivery of active components such as pharmaceutical and neutraceutical components, or a combination of any of the foregoing. Examples of ophthalmic devices include lenses and optical and ocular inserts, including, but not limited to punctal plugs and the like.

As used herein, the term "lens" refers to ophthalmic devices that reside in or on the eye. The term lens includes but is not limited to soft contact lenses, hard contact lenses, intraocular lenses, overlay lenses.

The medical devices, ophthalmic devices and lenses of the present invention are, in one embodiment, made from silicone elastomers or hydrogels, which include but are not limited to silicone hydrogels, and silicone-fluorohydrogels. These hydrogels contain hydrophobic and hydrophilic monomers that are covalently bound to one another in the cured lens.

As used herein "uptake" means associated in, with or on the lens, deposited in or on the lens. "Percent (%) uptake" of polycationic components means the percent of the polycationic component which associates in, with or on the lens or deposits in or on the lens compared to the total amount of that polycationic component in the ophthalmic solution prior to contact with the silicone hydrogels of the present invention.

As used herein "reactive mixture" refers to the mixture of components (both reactive and non-reactive) which are mixed together and subjected to polymerization conditions to form the ionic silicone hydrogels of one embodiment of the present invention. The reactive mixture comprises reactive components such as monomers, macromers, prepolymers, cross-linkers, initiators, diluents and additives such as wetting agents, release agents, dyes, light absorbing compounds such as UV absorbers and photochromic compounds, any of which may be reactive or non-reactive but are capable of being retained within the resulting medical device, as well as pharmaceutical and nutriceutical compounds. It will be appreciated that a wide range of additives may be added based upon the medical device which is made, and its intended use. Concentrations of components of the reactive mixture are given in weight % of all components in the reaction mixture, excluding diluent. When diluents are used their concentrations are given as weight % based upon the amount of all components in the reaction mixture and the diluent.

As used herein a statistical copolymer is a polymer having at least one segment formed from reactive components having substantially similar reaction rate constants, k for reaction with themselves and with each other. For example, statistical copolymers include crosslinked polymer matrices which are formed from reactive components having the same reactive functionality, polymers formed from reactive components having the same reactive functionality and block copolymers where at least one block is formed from reactive components having the same reactive functionality. Generally, substantially similar reaction rate constants are within about 10%. Reactive components which have the same reactive functionality have substantially similar reaction rate constants.

As used herein, cationic tear components include cationic proteins including lactoferrin, lysozyme, serum albumin, and secretory immunoglobulin A. Lysozyme is a preferred cationic tear component.

As used herein, ophthalmic solutions are solutions which are instilled in the eye or are used to condition or clean devices which are placed in the ocular environment. Examples of ophthalmic solutions include eye drops, rewetting drops, contact lens multipurpose solutions, packaging solutions for ophthalmic devices, including contact lenses.

Contact lens multipurpose solutions frequently contain polycationic components. Polycationic components include positively charged organic compounds, such as cationic water soluble polymeric ammonium salts, such as biguanides, bisbiguanides and polyquaternium containing compounds, also called "polyquats" or PQ compounds. Polyhexamethylene biguanide (PHMB) is a common biguanide used in contact lens, multipurpose, cleaning and care solutions. Examples of water soluble polymeric ammonium salts include polycationic polymers having quartenary ammonium centers. Examples include PQ-1, PQ-42 (poly[oxyethylene(dimethyliminio)ethylene (dimethyliminio)ethylene dichloride]), and the like. Cationic water soluble polymeric tetraalkyl phosphonium salts may also be used in place of the ammonium salts. Non-polymeric cationic organic components having two or more cations such as chlorhexidine (N',N''''-hexane-1,6-diylbis[N-(4-chlorophenyl)(imidodicarbonimidic diamide)], or CHG), and the like may also be included. Inorganic charged ions, such as sodium ions are not cationic components as defined herein.

PQ1 is a cationic copolymer having quartenary ammonium ions in its polymer backbone. Specifically PQ1 is poly[(dimethyliminio)-2-butene-1,4-diyl chloride (1:1)], α-[4-[tris(2-hydroxyethyl)ammonio]-2-buten-1-yl]-ω-[tris(2-hydroxyethyl)ammonio]-, chloride (CAS 75345-27-6). Contact lens solutions, including multipurpose solutions and cleaning solutions, generally also contain citrates such as citrate dihydrate and citric acid monohydrate to help prevent PQ1 uptake by contact lenses. However, the addition of anionicity to silicone hydrogel lenses can result in undesirable PQ1 uptake by the lens, even in the presence of citrates. In another embodiment, the present invention further provides desirably low uptake of water soluble polymeric ammonium salts.

RAFT refers to reversible addition fragmentation-chain transfer polymerization, a form of "pseudo-living" free radical polymerization.

Hydrophilic components are components that are at least 10% soluble in water. So, if 10 weight parts of the monomer are combined with 90 weight parts of water, a clear, single phase solution is formed with mixing at room temperature.

Anionic components are components comprising at least one anionic group and at least one reactive group. Anionic groups are groups which bear a negative charge at neutral pH. Examples of anionic groups include carboxylate groups, phosphates, sulphates, sulphonates, phosphonates, borates, mixtures thereof and the like. In one embodiment the anionic components comprise three to ten carbon atoms, and in another, three to eight carbon atoms. In an embodiment the anionic groups comprise carboxylate groups or sulphonate groups. Anionic components also include ionizable salts of any of the foregoing, for examples salts containing calcium, sodium, lithium, magnesium and mixtures thereof.

Reactive functionality or groups include those that can undergo chain reaction polymerizations, such as free radical and/or cationic polymerization under polymerization conditions. It is also possible to synthesize silicone copolymers via step reaction polymerization such as polyesters from the reaction of diols and diacids and polyurethanes from the reaction of diols and di-isocyanates or via thiol-ene reactions. In general, polymerizable groups can be classified as activated or unactivated polymerizable groups.

Activated polymerizable components are those that have at least two double bonds in conjugation:

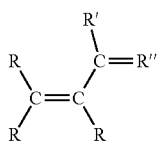

R are independently selected from H, carboxyl groups, ester groups, halides groups, $C_1$-$C_4$ alkyl groups, which may be further substituted with carboxylic acid or ester groups. In another embodiment R is selected from H and unsubstituted —$C_{1-4}$ alkyl groups; and in another embodiment from H and methyl, —COOH, —$CH_2COOH$, in another embodiment H and —$CH_3$;

R' is O or N which is further substituted a group selected from H, $C_{1-3}$ alkyl groups which may be further substituted with hydroxyl groups, carboxyl groups or carboxyester groups; or R' may be an alkenylene, which taken with R" forms a phenyl ring. In one embodiment R' is O or N substituted with H or unsubstituted $C_{1-3}$ alkyl.

R" is O or an alkenylene which when taken with R' forms a phenyl ring.

Examples of activated polymerizable groups include acrylate or methacrylate esters, itaconic acid esters, fumaric or maleic acid esters, acrylamides or methacrylamides, or styrenes.

Unactivated polymerizable groups have a carbon-carbon double bond, but do not have a second double bond in conjugation:

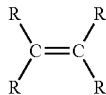

in which each R may be H, $C_1$-$C_4$ alkyl groups which may be unsubstituted or substituted with hydroxyl, carboxy, carboxyester, Cl, Br, O, or $N(R^2)COR^3$, $R^2$ is H or $COR^3$, unsubstituted C1-3 alkyl, $R^3H$ or unsubstituted C1-3, and Rx and Ry may together be propylene, O may be substituted with C1-3 alkyl or CORx provided that the atom bonded to the carbon-carbon bond is not itself doubly or triply bonded. Examples of unactivated polymerizable groups include vinyl lactams, vinyl amides, vinyl carbonates, vinyl carbamates, allyl ethers, allyl alcohols and the like.

Non-limiting examples of free radical reactive groups include (meth)acrylates, styryls, vinyls, vinyl ethers, $C_{1-6}$alkyl(meth)acrylates, (meth)acrylamides, $C_{1-6}$alkyh-meth)acrylamides, N-vinyllactams, N-vinylamides, $C_{2-12}$alkenyls, $C_{2-12}$alkenylphenyls, $C_{2-12}$alkenylnaphthyls, $C_{2-6}$alkenylphenylC$_{1-6}$alkyls, O-vinylcarbamates and O-vinylcarbonates. Non-limiting examples of cationic reactive groups (groups that can polymerize under cationic polymerization conditions) include vinyl ethers or epoxide groups and mixtures thereof. In one embodiment the reactive groups comprises (meth)acrylate, acryloxy, (meth)acrylamide, and mixtures thereof.

Any chemical name preceded by (meth), for example (meth)acrylate, includes both the unsubstituted and methyl substituted compound.

A statistical copolymer is formed between reactive comonomers, for example A and B, when their reactivity ratios, $r_A$ and $r_B$, approximate each other and approach unity. The "statistical" or "non-statistical" copolymerization of these two monomers is characterized by the relative mole fractions of monomers A and B that incorporate into the backbone of the copolymer as it is undergoing polymerization. The mole fraction of monomer A, $F_A$, incorporated into a copolymer of A and B, for example, is predicted by the Mayo-Lewis Equation:

$$F_A = \frac{r_A f_A^2 + f_A f_B}{r_A f_A^2 + 2f_A f_B + r_B f_B^2}$$

where $$r_A = \frac{k_{AA}}{k_{AB}}, r_B = \frac{k_{BB}}{k_{BA}},$$

and $f_A$ and $f_B$ are the relative mole fractions of A and B. The reactivity ratios, $r_A$ and $r_B$, are defined by four propagation rate constants, $k_{AA}$, $k_{AB}$, $k_{BA}$, and $k_{BB}$. For a propagating copolymer in a comonomer mixture of A and B, there are four possible radical addition scenarios that yield four distinct propagation rate constants:

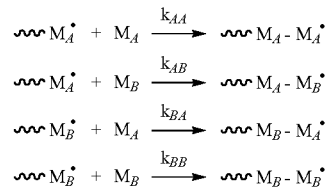

Generally, the relative values of $r_A$ and $r_B$, the mole fractions of both monomers, and the extent of conversion of the copolymerization are the major factors which dictate the microstructure of the resultant copolymer. In general there are limiting cases for $r_A$ and $r_B$ that apply specifically to the invention disclosed herein. In cases where $r_A$ and $r_B$ are equal and approach unity (e.g. $r_A=r_B\approx1$) the copolymerization is considered to be "random" or "statistical," i.e. there is an equal probability that monomer A will add to itself and to monomer B, and monomer B will add to itself and monomer A with equal probability also. In one embodiment "similar" reactivity ratios are those for which the reactivity ratios of the fastest and slowest reactive components in the reactive mixture are within 25% of each other, and in another embodiment within about 10% of each other, and in another embodiment within about 5% of each other. In some embodiments minor reactive additives, such as reactive dyes or UV absorbers can have reactivity ratios which are greater than the herein disclosed ranges. The reactivity ratios may be determined by measuring the relative depletion of monomer A and B from the polymerization solution and the relative incorporation of A and B into the resultant copolymer. This measurement is taken at low total monomer conversion, i.e. around 10-20%, and is repeated across a range of initial monomer compositions between 1-99% A or 99-1% B.

In another embodiment, the random or statistical copolymers are formed from charged monomers and other monomers comprising the same reactive double-bonds (anionic charge-bearing acrylamido-monomers being paired with other acrylamido-comonomers or anionic charge-bearing methacrylic-monomers being paired with other methacrylate-comonomers). As shown by the Examples herein, the consumption of charge-bearing monomers with other monomers that contain the same reactive functionality produce lenses which display the desired selective uptake of cationic tear components, such as lysozyme over polycationic components, such as PQ1. Reactive mixtures comprising reactive components having the same reactive functionality and similar reactivity ratios (that approach unity), which produce the homogeneous distribution of charge across the surface and throughout the bulk of the lens.

Where $r_A=r_B\approx0$, the probabilities of monomers A and B adding to themselves is very low. This results in the formation of alternating copolymers of A and B, and lens materials having the desired distribution of charge throughout the lens and the desired selective uptake of cationic tear components over polycationic components.

Where $r_A>1>r_B$, statistical copolymers of the present invention are not formed. In this case early in the polymerization, monomer A is consumed at a higher rate than monomer B. At this early point in the copolymerization, copolymers that are formed are very rich in monomer A. As the polymerization progresses and monomer A is depleted over monomer B, thus changing the relative mole fractions in favor of monomer B, the copolymer microstructure shifts from being rich in monomer A to rich in monomer B. This occurs until all or most of monomer A is consumed, at which point the polymer that is formed is completely or mostly composed of monomer B. This is also known to those skilled in the art as "compositional drift." In a comparative example of this invention, an anionic acrylamido-monomer is copolymerized in a mixture of methacrylates and other acrylamides to make a contact lens or medical device. In this case, it is believed that the methacrylates are consumed at a much higher rate, compared to the acrylamido-monomers early in the polymerization. This continues until all or most of the methacrylates are consumed, after which point the acrylamido-monomers are consumed and the polymerization reaches 100% conversion. Because the anionic charge-bearing acrylamido-monomer has a much higher probability of being consumed later in the reaction, the charge in and on the bulk and surface of the substrate is not homogeneously distributed throughout the polymer bulk. This leads to a significant amount of PQ1 uptake as well as lysozyme, which is undesirable.

When $r_A=r_B>1$, blocky-type copolymers are formed. In this case monomer A has a high probability of adding to itself over monomer B and monomer B has a high probability of adding to itself over monomer A. In extreme cases, where A would rarely add to B and vice versa, i.e. where $r_A=r_B>>1$, formation of a mixture of homopolymers is anticipated. These cases are believed to produce a heterogeneous distribution of charge in and on the resulting substrate.

It has been found that by selecting the components of the reactive mixture such that reactivity rates are substantially matched, statistical copolymers can be made wherein the units from the anionic monomers are randomly distributed throughout either the polymer or at least one segment of the polymer, depending upon the embodiment of the present invention. The random distribution of negative charge throughout the polymer is believed to provide a delocalization of charge, which provides increased uptake by the polymer of beneficial proteins such as lysozyme, but low uptake of positively charged components in contact lens solutions, including polyquarternium salts, such as, but not limited to PQ1.

Thus, in one embodiment the non-ionic hydrophilic monomer and the anionic monomer are either both activated or both unactivated. In another embodiment the reactive functionality for both the non-ionic hydrophilic monomer and the anionic monomer are the same, for example both the non-ionic hydrophilic monomer and the anionic monomer are both are methacrylates. In another embodiment both the non-ionic hydrophilic monomer and the anionic monomer are methacrylamides. Non-limiting examples of such combinations are included in the Examples below.

Examples of suitable anionic components include reactive carboxylic acids, including alkylacrylic acids, such as (meth)acrylic acid, acrylic acid, itaconic acid, crotonic acid, cinnamic acid, vinylbenzoic acid, fumaric acid, maleic acid, monoesters of fumaric acid, maelic acid and itaconic acid; 3-acrylamidopropionic acid, 4-acrylamidobutanoic acid, 5-acrylamidopentanoic acid, N-vinyloxycarbonyl-α-alanine, N-vinyloxycarbonyl-β-alanine (VINAL), 2-vinyl-4,4-dimethyl-2-oxazolin-5-one (VDMO), reactive sulphonate salts, including sodium-2-(acrylamido)-2-methylpropane sulphonate, 3-sulphopropyl (meth)acrylate potassium salt, 3-sulphopropyl (meth)acrylate sodium salt, bis 3-sulphopropyl itaconate di sodium, bis 3-sulphopropyl itaconate di potassium, vinyl sulphonate sodium salt, vinyl sulphonate salt, styrene sulphonate, 2-sulphoethyl methacrylate and mixtures thereof and the like. In one embodiment the anionic component is selected from reactive carboxylic acids, in another from methacrylic acid and N-vinyloxycarbonyl alanine. In another embodiment, where the reactive monomers comprise acrylamido reactive groups the anionic monomer comprises an acrylamide acid, such as 3-acrylamidopropionic acid, 4-acrylamidobutanoic acid, 5-acrylamidopentanoic acid, 2-acrylamido-2-methylpropane sulphonic acid, salts of said acrylamido acids and combinations thereof. Suitable salts include ophthalmically compatible salts including sodium, potassium and calcium salts.

It has been surprisingly found that the acrylamido sulphonic acid or acrylamido sulphonic acid salts are compatible with the all acrylamide formulations of the present invention. The acrylamido sulphonic acid or acrylamido sulphonic acid salts are generally too polar to be soluble in silicone hydrogel reactive mixtures, even at the low molar concentrations disclosed herein. However, when the single reactive functionality is methacrylamide acrylamido sulphonic acid or acrylamido sulphonic acid salt may be directly incorporated into the reactive mixture in amounts up to about 5 mole %, in some embodiments up to about 3 mol %, and in other embodiments between about 0.1 to about 2 mol %.

In another embodiment the reactive components comprise methacrylate groups and the ionic component comprises methacrylic acid. It is understood that these monomers may be copolymerized in a non-ionic (ester) form, and then deprotonated or hydrolyzed to form ionic groups in the final product.

Those of skill in the art will understand that the foregoing anionic monomers are selected based upon the functionality of the other reactive components. For example, when the major polymerizable components comprise acrylamide reactive functionality the anionic monomer may be 3-acrylamidopropionic acid, 4-acrylamidobutanoic acid, 5-acrylamidopentanoic acid, sodium-2-(acrylamido)-2-methylpropane sulphonate, 2-acrylamido-2-methylpropane sulfonic acid and combinations thereof.

When the major polymerizable components comprise (meth)acrylate functionality the anionic monomer may be (meth)acrylic acid, itaconic acid, crotonic acid, cinnamic acid, fumaric acid, maleic acid, monoesters of fumaric acid, 3-sulphopropyl (meth)acrylate potassium salt, 3-sulphopropyl (meth)acrylate sodium salt, bis 3-sulphopropyl itaconate di sodium, bis 3-sulphopropyl itaconate di potassium, sulphoethyl methacrylate, and mixtures thereof. In another embodiment the major polymerizable components comprise (meth)acrylate functionality, and the anionic monomer may be (meth)acrylic acid, 3-sulphopropyl (meth)acrylate potassium salt, 3-sulphopropyl (meth)acrylate sodium salt, sulphoethyl methacrylate, and mixtures thereof.

When the major polymerizable components comprise vinyl functionality the anionic monomer may be N-vinyloxycarbonyl-α-alanine, N-vinyloxycarbonyl-β-alanine, 2-vinyl-4,4-dimethyl-2-oxazolin-5-one, vinyl sulphonate sodium salt, vinyl sulphonate salt, and mixtures thereof.

Suitable non-ionic hydrophilic monomers include N,N-dimethyl acrylamide (DMA), 2-hydroxyethyl methacrylate (HEMA), glycerol methacrylate, 2-hydroxyethyl methacrylamide, polyethyleneglycol monomethacrylate, N-vinyl amides, N-vinyl lactams (e.g. NVP), N-vinyl-N-methyl acetamide, N-vinyl-N-ethyl acetamide, N-vinyl-N-ethyl formamide, N-vinyl formamide. Vinyl carbonate or vinyl carbamate monomers, such as those disclosed in U.S. Pat. No. 5,070,215, and the hydrophilic oxazolone monomers disclosed in U.S. Pat. No. 4,910,277 may also be used.

The hydroxyl-containing (meth)acrylamide monomers of Formula c0, disclosed in US 2011-0230589 A1 may also be used:

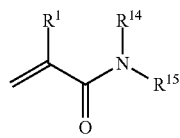
(c0)

wherein, $R^1$ is hydrogen or methyl; at least one of $R^{14}$ and $R^{15}$ is substituted with a C1-C20 alkyl substituted with at least one hydroxyl group, with the proviso that when i) one of $R^{14}$ and $R^{15}$ is hydrogen, ii) the other of $R^{14}$ and $R^{15}$ is a C1-C20 alkyl group substituted with two or more hydroxyl groups. In one embodiment, the non-silicone (meth)acrylamide monomer comprises two or more hydroxyl groups in the molecule. In some embodiments R1 is a hydrogen atom and at least one of $R^{14}$ and $R^{15}$ is selected from hydrogen, optionally substituted C1-C20 alkyl group, or optionally substituted C6-C20 aryl group with the proviso that the total number of hydroxyl groups in $R^{14}$ and R'5 is two or more. In one embodiment $R^{14}$ and $R^{15}$ is are independently selected from C1-C10 alkyl group which may be substituted with at least one more hydroxyl group, and in other embodiments C1-C6 alkyl group which may be substituted with at least one more hydroxyl group, so long as the hydrophilic (meth)acrylamide meets the proviso above.

Examples of $R^{14}$ and $R^{15}$ include hydrogen atoms, methyl groups, ethyl groups, propyl groups, n-propyl groups, i-propyl groups, n-butyl groups, s-butyl groups, t-butyl groups, n-pentyl groups, i-pentyl groups, s-pentyl groups, neopentyl groups, hexyl groups, heptyl groups, octyl groups, nonyl groups, decyl groups, dodecyl groups, eicosyl groups, phenyl groups, naphthyl groups, 2-hydroxyethyl groups, 2-hydroxypropyl groups, 3-hydroxypropyl groups, 2,3-dihydroxypropyl groups, 4-hydroxy butyl groups, 2-hydroxy-1,1-bis(hydroxymethyl) ethyl groups, 2-hydroxymethylphenyl groups, 3-hydroxymethylphenyl groups, 4-hydroxymethylphenyl groups and the like. These alkyl and hydroxyalkyl groups can be straight or branched.

A particularly preferable example of a non-silicone type (meth)acrylamide monomer containing two or more hydroxyl groups in the molecule include the monomers expressed by the following general formulae (c1) through (c3).

[FORMULA 10]

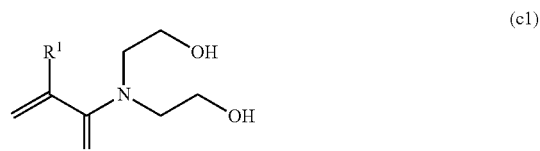
(c1)

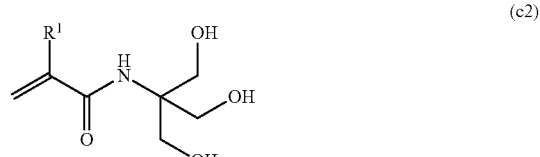
(c2)

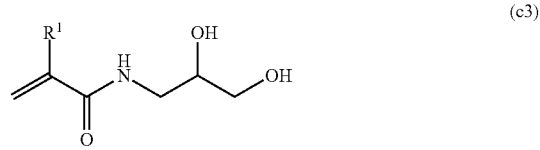
(c3)

In chemical formulae (c1) through (c3), $R^1$ independently represents a hydrogen atom or a methyl group.

In another embodiment, the hydroxyl-containing (meth)acrylamide monomer comprises one hydroxyl group and no amide hydrogen in the molecule. In chemical formula (c0) of this embodiment, $R^1$ represents methyl and $R^{14}$ and $R^{15}$ are independently selected from optionally substituted C1-C20 alkyl group, or optionally substituted C6-C20 aryl group with the proviso that one of $R^{14}$ and $R^{15}$ is substituted with at least one hydroxyl group. Examples of $R^{14}$ and $R^{15}$ include methyl groups, ethyl groups, propyl groups, n-propyl groups, i-propyl groups, n-butyl groups, s-butyl groups, t-butyl groups, n-pentyl groups, i-pentyl groups, s-pentyl groups, neopentyl groups, hexyl groups, heptyl groups, octyl groups, nonyl groups, decyl groups, dodecyl groups, eicosyl groups, phenyl groups, naphthyl groups, 2-hydroxyethyl groups, 2-hydroxypropyl groups, 3-hydroxypropyl groups, 4-hydroxy butyl groups, 2-hydroxymethylphenyl groups, 3-hydroxymethylphenyl groups, 4-hydroxymethylphenyl groups and the like. These alkyl groups can be straight or branched. Examples of hydroxyl-containing acrylamide monomer of this embodiment include the monomers expressed by the following general formulae (c11) through (c13).

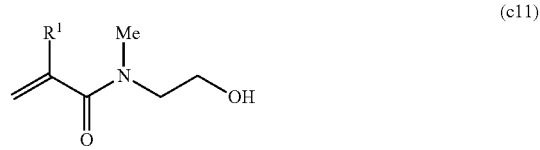
(c11)

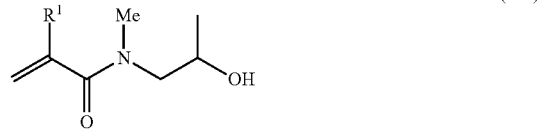
(c12)

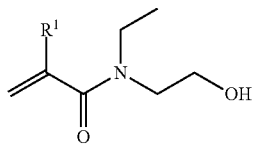

In chemical formulae (c11) through (c13), $R^1$ independently represents a methyl group.

In some embodiments acrylamide monomer comprising one hydroxyl group and one amide hydrogen in the molecule may be used. Examples of a mono-hydroxyl functionalized acrylamide monomer include N-(mono-hydroxyl substituted C1-C20 alkyl)acrylamide and N-(mono-hydroxyl substituted C6-C20 aryl)acrylamide. More specific examples include N-(2-hydroxyethyl)acrylamide, N-(2-hydroxypropyl)acrylamide, N-(3-hydroxypropyl)acrylamide, N-(2-hydroxybutyl)acrylamide, N-(3-hydroxybutyl)acrylamide, N-(4-hydroxy butyl)acrylamide, N-(2-hydroxymethylphenyl)acrylamide, N-(3-hydroxymethylphenyl)acrylamide, N-(4-hydroxymethylphenyl)acrylamide and the like. In some embodiments, N-(mono-hydroxyl substituted C2-C4 alkyl)acrylamide and particularly N-(2-hydroxyethyl)acrylamide may be preferred.

The amount of the anionic monomer is also important. Even when a desirable charge distribution has been achieved, if the concentration of the anionic monomer is too high, undesirable PQ-1 uptake may occur. Thus, in embodiment, where the anionic monomer is a component of a reusable silicone hydrogel contact lens, the anionic monomer may be included in amounts up to about 5 mol %, in some embodiments between about 0.1 and about 5 mol %, between about 0.1 and about 4 mol %, and in other embodiments between about 0.2 and about 4 mol %. In embodiments where the contact lens is worn for only a single day and then thrown away, higher amounts of the anionic monomer may be included. The upper limit for the anionic monomer in these embodiments may be selected to provide the desired level of lysozyme or other team components, and a water content of less than about 70% water, in some embodiments less than 70% water, and in others less than about 65% water.

The anionic monomer and non-ionic hydrophilic monomer may be copolymerized (either alone or with additional components) to form a water soluble, uncrosslinked polymer or may be included in a silicone hydrogel reaction mixture and cured to form the silicone hydrogel contact lens.

When the anionic monomer and non-ionic, hydrophilic monomer are copolymerized to form an uncrosslinked statistical copolymer, the anionic monomer is present in the uncrosslinked statistical copolymer in amounts between about 20 to about 80 mol %, and in some embodiments between about 20 to about 60 mol %. The non-ionic, hydrophilic monomer may be present in amounts between about 80 to about 20 mol % and in some embodiments between about 80 to about 40 mol %. If the polymer contains a hydrophobic segment or block, as described below, these mol % are based upon the hydrophilic segment of the polymer only.

The hydrophilic segment of the uncrosslinked statistical copolymers of the present invention have a degree of polymerization of at least about 300.

The uncrosslinked statistical copolymers may be formed by a number of methods including, but not limited to, step growth polymerization, such as thiol-ene chemistry, and chain reaction polymerization, such as free radical polymerization and RAFT.

In one embodiment the uncrosslinked statistical copolymer further comprises a hydrophobic block on at least one terminal end of the uncrosslinked statistical copolymer. The hydrophobic block may be a hydrocarbon block, a siloxane block, or any other block which is capable of associating with the silicone hydrogel contact lens. In another embodiment the uncrosslinked statistical copolymer has a hydrophobic block which is capable of associating with another polymeric biomedical device such as a stent, a rigid contact lens, a catheter, stent or other implant.

In one embodiment, the hydrophobic block comprises polydialkylsiloxane, polydiarylsiloxane and mixtures thereof. The alkyls may be independently selected from $C_1$-$C_4$ alkyl, and in one embodiment the hydrophobic block comprises polydimethylsiloxane or polydiethylsiloxane, either of which may be terminated by a $C_{1-12}$ alkyl, $C_1$-$C_4$ alkyl, aryl or in some embodiments methyl or n-butyl.

The hydrophobic block may comprise between about 6 and about 200 siloxy units, between about 6 and about 60 siloxy units, 6 and about 20 siloxy units, 6-15 siloxy units and 6 to 12 siloxy units.

The uncrosslinked, statistical copolymers may be dissolved in solutions which swell the medical device and contacted with the medical device. In one embodiment where the device is a silicone hydrogel contact lens the uncrosslinked, statistical copolymers are dissolved in water or an aqueous solution and contacted with the contact lens during processing, packaging or cleaning or storage of the lens. For example the uncrosslinked, statistical copolymers may be incorporated into a hydration or packaging solution or may be included in a multipurpose or cleaning solution which is used by the contact lens wearer.

The amount of uncrosslinked, statistical copolymers included in the solutions will depend in part on the concentration of the anionic monomer in the uncrosslinked, statistical copolymers. For example, uncrosslinked, statistical copolymers containing 30 mol % anionic monomer can be added in higher amounts than uncrosslinked, statistical copolymers having 80 mol % anionic monomer, as is shown the Examples. It is desirable to balance the concentration of anionic monomer in the uncrosslinked, statistical copolymers with the concentration of uncrosslinked, statistical copolymers in the solution to achieve the desired levels of lysozyme and PQ1 uptake. Concentrations of uncrosslinked, statistical copolymers of up to about 2000 ppm, and in some embodiments between about 20 ppm and 2000 ppm and in other embodiments between about 50 and about 1500 ppm are desirable.

In another embodiment the anionic monomer and the non-ionic hydrophilic monomer are included in the silicone hydrogel reactive mixture to form a silicone hydrogel polymer having a homogeneously distributed anionic charge throughout the polymer. In this embodiment the resulting contact lens has a contact angle of less than about 70°, less than about 50° and in some embodiments less than about 30° all as measured by sessile drop.

In this embodiment substantially all of the polymerizable components in the reaction mixture have the same reactive functionality. Non-reactive components, such as wetting agents may also be present. Contact lens formulations may contain small amounts of components, such as, but not limited to handling tints and UV absorbers, which because of their small concentration, do not need to have the same reactive functionality. Generally, the concentration of reactive components in the reaction mixture which have different functionality should be limited to less than about 0.5 mol %. Non-reactive components, such as non-reactive wetting agents may be present in greater amounts (up about 15 weight %, and in some embodiments up to about 20 weight %) as they do not participate in the reaction.

In this embodiment the anionic monomer is present in the reactive mixture in concentrations in amounts up to about 5 mol %, in some embodiments between about 0.1 and about 5 mol %, between about 0.1 and about 4 mol %, and in other embodiments between about 0.2 and about 4 mol %. The non-ionic hydrophilic monomer is present in amounts of at least about 10 wt %, and in some embodiments between about 10 wt % and about 70 wt %, between about 20 and about 60% and in other embodiments, between about 20 and about 50 weight %.

The reaction mixture further comprises at least one silicone-containing component. A silicone-containing component is one that contains at least one [—Si—O—] group, in a monomer, macromer or prepolymer. In one embodiment, the Si (silicon) and attached O are present in the silicone-containing component in an amount greater than 20 weight percent, and in another embodiment greater than 30 weight percent of the total molecular weight of the silicone-containing component. Useful silicone-containing components comprise polymerizable functional groups such as (meth)acrylate, (meth)acrylamide, N-vinyl lactam, N-vinylamide, and styryl functional groups. Examples of silicone-containing components which are useful in this invention may be found in U.S. Pat. Nos. 3,808,178; 4,120,570; 4,136,250; 4,153,641; 4,740,533; 5,034,461 and 5,070,215, and EP080539. All of the patents cited herein are hereby incorporated in their entireties by reference. These references disclose many examples of olefinic silicone-containing components.

Suitable silicone-containing components include compounds of Formula I

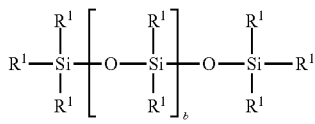

where $R^1$ is independently selected from monovalent reactive groups, siloxane chain, monovalent alkyl groups, or monovalent aryl groups. The monovalent alkyl and aryl groups further comprise functionality selected from hydroxy, amino, oxa, carboxy, alkyl carboxy, alkoxy, amido, carbamate, carbonate, halogen or combinations thereof; and monovalent siloxane chains comprising 1-100 Si—O repeat units which may further comprise functionality selected from alkyl, hydroxy, amino, oxa, carboxy, alkyl carboxy, ether, amido, carbamate, halogen or combinations thereof; where b=0 to 500, where it is understood that when b is other than 0, b is a distribution having a mode equal to a stated value;

wherein at least one $R^1$ comprises at least one monovalent reactive group, and in some embodiments between one and 3 $R^1$ comprise monovalent reactive groups.

As used herein "monovalent reactive groups" are groups that can undergo polymerization such as free radical, anionic and/or cationic polymerization. Non-limiting examples of free radical reactive groups include (meth)acrylates, styryls, vinyls, vinyl ethers, substituted or unsubstituted $C_{1-6}$alkyl (meth)acrylates, (meth)acrylamides, substituted or unsubstituted $C_{1-6}$alkyl(meth)acrylamides, N-vinyllactams, N-vinylamides, $C_{2-12}$alkenyls, $C_{2-12}$alkenylphenyls, $C_{2-12}$alkenylnaphthyls, $C_{2-6}$alkenylphenyl$C_{1-6}$alkyls, O-vinylcarbamates and O-vinylcarbonates. Suitable substituents on said C1-6 alkyls include ethers, hydroxyls, carboxyls, halogens and combinations thereof. Non-limiting examples of cationic reactive groups include vinyl ethers or epoxide groups and mixtures thereof. In one embodiment the free radical reactive groups comprises (meth)acrylate, acryloxy, (meth)acrylamide, and mixtures thereof.

Suitable monovalent alkyl and aryl groups include unsubstituted monovalent $C_1$ to $C_{1-6}$alkyl groups, $C_6$-$C_{14}$ aryl groups, such as substituted and unsubstituted methyl, ethyl, propyl, butyl, 2-hydroxypropyl, propoxypropyl, polyethyleneoxypropyl, combinations thereof and the like.

In one embodiment on $R^1$ is selected from $C_{1-6}$alkyl (meth)acrylates, and $C_{1-6}$alkyl(meth)acrylamides, which may be unsubstituted or substituted with hydroxyl, alkylene ether or a combination thereof. In another embodiment $R^1$ is selected from propyl(meth)acrylates and propyl (meth)acrylamides, wherein said propyl may be optionally substituted with hydroxyl, alkylene ether or a combination thereof.

In one embodiment b is zero, one $R^1$ is a monovalent reactive group, and at least 3 $R^1$ are selected from monovalent alkyl groups having one to 16 carbon atoms, and in another embodiment from monovalent alkyl groups having one to 6 carbon atoms. Non-limiting examples of silicone components of this embodiment include 2-methyl-,2-hydroxy-3-[3-[1,3,3,3-tetramethyl-1-[(trimethylsilyl)oxy]disiloxanyl]propoxy]propyl ester ("SiGMA"), 2-hydroxy-3-methacryloxypropyloxypropyl-tris(trimethylsiloxy)silane, 3-methacryloxypropyltris(trimethylsiloxy)silane ("TRIS"), 3-methacryloxypropylbis(trimethylsiloxy)methylsilane and 3-methacryloxypropylpentamethyl disiloxane.

In another embodiment, b is 2 to 20, 3 to 15 or in some embodiments 3 to 10; at least one terminal $R^1$ comprises at least one monovalent reactive group and the remaining $R^1$ are selected from monovalent alkyl groups having 1 to 16 carbon atoms, and in another embodiment from monovalent alkyl groups having 1 to 6 carbon atoms. In yet another embodiment, b is 3 to 15, one terminal $R^1$ comprises a monovalent reactive group selected from substituted or unsubstituted $C_{1-6}$alkyl(meth)acrylates, substituted or unsubstituted $C_{1-6}$alkyl(meth)acrylamides, the other terminal $R^1$ comprises a monovalent alkyl group having 1 to 6 carbon atoms and the remaining $R^1$ comprise monovalent alkyl group having 1 to 3 carbon atoms. Non-limiting examples of silicone components of this embodiment include (mono-(2-hydroxy-3-methacryloxypropyl)-propyl ether terminated, n-butyl terminated polydimethylsiloxane (400-1000 MW)) ("OH-mPDMS"), monomethacryloxypropyl terminated mono-n-butyl terminated polydimethylsiloxanes (800-1000 MW), ("mPDMS"), N-(2,3-dihydroxypropane)-N'-(propyl tetra(dimethylsiloxy) dimethylbutylsilane) acrylamide, and methacryamide silicones of the following formulae (s1) through (s6);

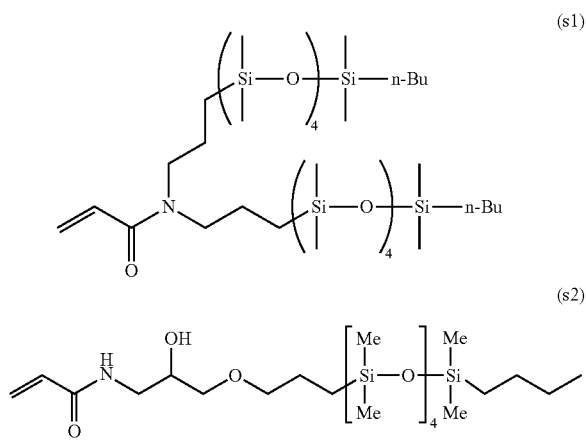

(s3)
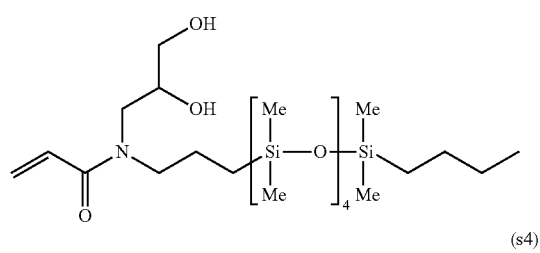

(s4)
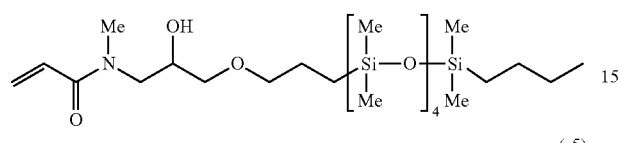

(s5)
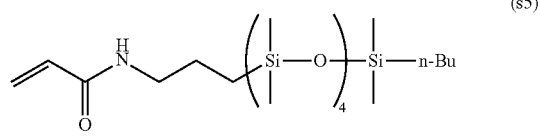

(s6)
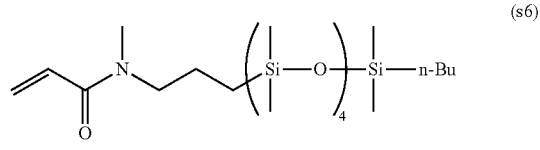

In another embodiment b is 5 to 400 or from 10 to 300, both terminal $R^1$ comprise monovalent reactive groups and the remaining $R^1$ are independently selected from monovalent alkyl groups having 1 to 18 carbon atoms which may have ether linkages between carbon atoms and may further comprise halogen.

In another embodiment, one to four $R^1$ comprises an allyl or vinyl carbonate or carbamate of the formula:

Formula XII

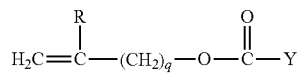

wherein: Y denotes O—, S— or NH—;

R denotes, hydrogen or methyl; d is 1, 2, 3 or 4; and q is 0 or 1.

The silicone-containing carbonate or carbamate monomers specifically include: 1,3-bis[4-(vinyloxycarbonyloxy) but-1-yl]tetramethyl-disiloxane; 3-(vinyloxycarbonylthio) propyl-[tris(trimethylsiloxy)silane]; 3-[tris(trimethylsiloxy) silyl]propyl allyl carbamate; 3-[tris(trimethylsiloxy)silyl] propyl vinyl carbamate; trimethylsilylethyl vinyl carbonate; trimethylsilylmethyl vinyl carbonate, and

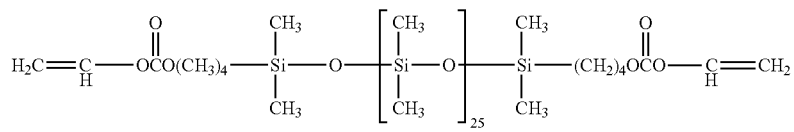

In another embodiment, where an acrylamide system is used, the (meth)acrylamide silicones of US2011/0237766 may be used with acrylamide hydrophilic monomers such as DMA and HEAA and acrylamide anionic monomers such as 3-acrylamidopropanoic acid (ACA1) or 5-acrylamidopentanoic acid (ACA2).

Where biomedical devices with modulus below about 200 are desired, only one $R^1$ shall comprise a monovalent reactive group and no more than two of the remaining $R^1$ groups will comprise monovalent siloxane groups.

In one embodiment, where a silicone hydrogel lens is desired, the lens of the present invention will be made from a reactive mixture comprising at least about 20 weight % and in some embodiments between about 20 and 70% wt silicone-containing components based on total weight of reactive monomer components from which the polymer is made.

Another class of silicone-containing components includes polyurethane macromers of the following formulae:

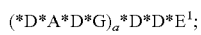

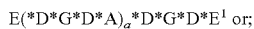

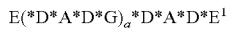

Formulae XIII-XV wherein:

D denotes an alkyl diradical, an alkyl cycloalkyl diradical, a cycloalkyl diradical, an aryl diradical or an alkylaryl diradical having 6 to 30 carbon atoms, G denotes an alkyl diradical, a cycloalkyl diradical, an alkyl cycloalkyl diradical, an aryl diradical or an alkylaryl diradical having 1 to 40 carbon atoms and which may contain ether, thio or amine linkages in the main chain;

* denotes a urethane or ureido linkage;

$a$ is at least 1;

A denotes a divalent polymeric radical of formula:

Formula XVI

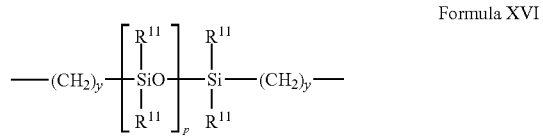

$R^{11}$ independently denotes an alkyl or fluoro-substituted alkyl group having 1 to 10 carbon atoms which may contain ether linkages between carbon atoms; y is at least 1; and p provides a moiety weight of 400 to 10,000; each of E and $E^1$ independently denotes a polymerizable unsaturated organic radical represented by formula:

Formula XVII

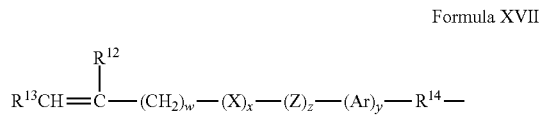

wherein: $R^{12}$ is hydrogen or methyl; $R^{13}$ is hydrogen, an alkyl radical having 1 to 6 carbon atoms, or a —CO—Y—$R^{15}$ radical wherein Y is —O—, Y—S— or —NH—; $R^{14}$ is a divalent radical having 1 to 12 carbon atoms; X denotes —CO— or —OCO—; Z denotes —O— or —NH—; Ar denotes an aromatic radical having 6 to 30 carbon atoms; w is 0 to 6; x is 0 or 1; y is 0 or 1; and z is 0 or 1.

In one embodiment the silicone-containing component comprises a polyurethane macromer represented by the following formula:

Formula XVIII

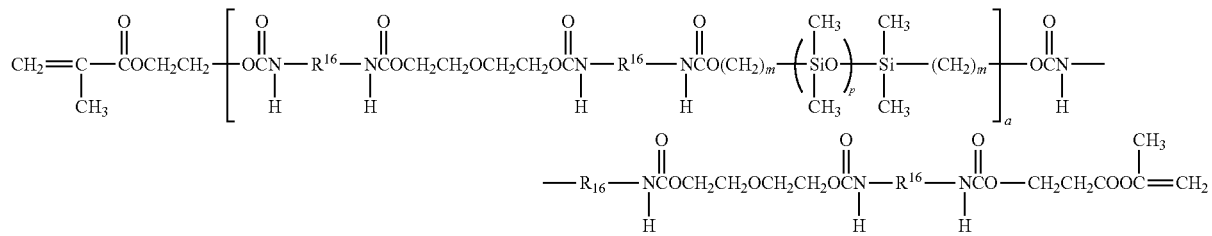

wherein $R^{16}$ is a diradical of a diisocyanate after removal of the isocyanate group, such as the diradical of isophorone diisocyanate. Another suitable silicone containing macromer is compound of formula X (in which x+y is a number in the range of 10 to 30) formed by the reaction of fluoroether, hydroxy-terminated polydimethylsiloxane, isophorone diisocyanate and isocyanatoethylmethacrylate.

desired balance of oxygen transmissibility and modulus it is preferred that all components having more than one polymerizable functional group ("multifunctional components") make up no more than 10 mmol/100 g of the reactive components, and preferably no more than 7 mmol/100 g of the reactive components.

In another embodiment, the reaction mixtures are substantially free of silicone containing components which contain trimethylsiloxy groups.

The silicone containing components may be present in amounts up to about 85 weight %, and in some embodiments between about 10 and about 80 and in other embodiments Formula XIX

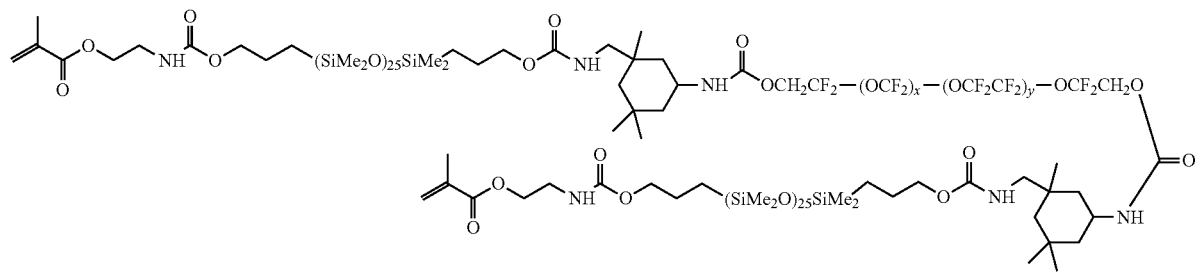

Other silicone-containing components suitable for use in this invention include those described is WO 96/31792 such as macromers containing polysiloxane, polyalkylene ether, diisocyanate, polyfluorinated hydrocarbon, polyfluorinated ether and polysaccharide groups. Another class of suitable silicone-containing components includes silicone containing macromers made via GTP, such as those disclosed in U.S. Pat. Nos. 5,314,960, 5,331,067, 5,244,981, 5,371,147 and 6,367,929. U.S. Pat. Nos. 5,321,108; 5,387,662 and 5,539,016 describe polysiloxanes with a polar fluorinated graft or side group having a hydrogen atom attached to a terminal difluoro-substituted carbon atom. US 2002/0016383 describe hydrophilic siloxanyl methacrylates containing ether and siloxanyl linkanges and crosslinkable monomers containing polyether and polysiloxanyl groups. Any of the foregoing polysiloxanes can also be used as the silicone-containing component in this invention.

In one embodiment of the present invention where a modulus of less than about 120 psi is desired, the majority of the mass fraction of the silicone-containing components used in the lens formulation should contain only one polymerizable functional group ("monofunctional silicone containing component"). In this embodiment, to insure the between about 20 and about 70 weight %, based upon all reactive components.

Other components that can be present in the reaction mixture used to form the contact lenses of this invention include wetting agents, such as those disclosed in U.S. Pat. No. 6,367,929, WO03/22321, WO03/22322, compatibilizing components, such as those disclosed in US2003/162862 and US2003/125498, ultra-violet absorbing compounds, medicinal agents, antimicrobial compounds, copolymerizable and nonpolymerizable dyes, including photochromic dyes, release agents, reactive tints, pigments, pharmaceutical and nutriceutical compounds, combinations thereof and the like. The sum of additional components may be up to about 20 wt %. In one embodiment the reaction mixtures comprise up to about 18 wt % wetting agent, and in another embodiment, between about 5 and about 18 wt % wetting agent.

A polymerization catalyst may be included in the reaction mixture. The polymerization initiators includes compounds such as lauroyl peroxide, benzoyl peroxide, isopropyl percarbonate, azobisisobutyronitrile, and the like, that generate free radicals at moderately elevated temperatures, and photoinitiator systems such as aromatic alpha-hydroxy ketones, alkoxyoxybenzoins, acetophenones, acylphosphine oxides, bisacylphosphine oxides, and a tertiary amine plus a diketone, mixtures thereof and the like. Illustrative examples of photoinitiators are 1-hydroxycyclohexyl phenyl ketone, 2-hydroxy-2-methyl-1-phenyl-propan-1-one, bis(2,6-dimethoxybenzoyl)-2,4-4-trimethylpentyl phosphine oxide (DMBAPO), bis(2,4,6-trimethylbenzoyl)-phenyl phosphineoxide (Irgacure 819), 2,4,6-trimethylbenzyldiphenyl phosphine oxide and 2,4,6-trimethylbenzoyl diphenylphosphine oxide, benzoin methyl ester and a combination of camphorquinone and ethyl 4-(N,N-dimethylamino)benzoate. Commercially available visible light initiator systems include Irgacure 819, Irgacure 1700, Irgacure 1800, Irgacure 819, Irgacure 1850 (all from Ciba Specialty Chemicals) and Lucirin TPO initiator (available from BASF). Commercially available UV photoinitiators include Darocur 1173 and Darocur 2959 (Ciba Specialty Chemicals). These and other photoinitators which may be used are disclosed in Volume III, Photoinitiators for Free Radical Cationic & Anionic Photopolymerization, $2^{nd}$ Edition by J. V. Crivello& K. Dietliker; edited by G. Bradley; John Wiley and Sons; New York; 1998. The initiator is used in the reaction mixture in effective amounts to initiate photopolymerization of the reaction mixture, e.g., from about 0.1 to about 2 parts by weight per 100 parts of reactive monomer. Polymerization of the reaction mixture can be initiated using the appropriate choice of heat or visible or ultraviolet light or other means depending on the polymerization initiator used. Alternatively, initiation can be conducted without a photoinitiator using, for example, e-beam. However, when a photoinitiator is used, the preferred initiators are bisacylphosphine oxides, such as bis(2,4,6-trimethylbenzoyl)-phenyl phosphine oxide (Irgacure 819®) or a combination of 1-hydroxycyclohexyl phenyl ketone and bis(2,6-dimethoxybenzoyl)-2,4-4-trimethylpentyl phosphine oxide (DMBAPO), and in another embodiment the method of polymerization initiation is via visible light activation. A preferred initiator is bis(2,4,6-trimethylbenzoyl)-phenyl phosphine oxide (Irgacure 819®).

The reactive components (silicone containing component, hydrophilic monomers, wetting agents, and other components which are reacted to form the lens) are mixed together either with or without a diluent to form the reaction mixture.

In one embodiment a diluent is used having a polarity sufficiently low to solubilize the non-polar components in the reactive mixture at reaction conditions. One way to characterize the polarity of the diluents of the present invention is via the Hansen solubility parameter, $\delta p$. In certain embodiments, the $\delta p$ is less than about 10, and preferably less than about 6. Suitable diluents are further disclosed in U.S. Ser. No. 60/452,898 and U.S. Pat. No. 6,020,445.

Classes of suitable diluents include, without limitation, alcohols having 2 to 20 carbons, amides having 10 to 20 carbon atoms derived from primary amines, ethers, polyethers, ketones having 3 to 10 carbon atoms, and carboxylic acids having 8 to 20 carbon atoms. For all solvents, as the number of carbons increase, the number of polar moieties may also be increased to provide the desired level of water miscibility. In some embodiments, primary and tertiary alcohols are preferred. Preferred classes include alcohols having 4 to 20 carbons and carboxylic acids having 10 to 20 carbon atoms.

In one embodiment the diluents are selected from 1,2-octanediol, t-amyl alcohol, 3-methyl-3-pentanol, decanoic acid, 3,7-dimethyl-3-octanol, tripropylene glycol methyl ether (TPME), butoxy ethyl acetate, mixtures thereof and the like.

In one embodiment the diluents are selected from diluents that have some degree of solubility in water. In some embodiments at least about three percent of the diluent is miscible water. Examples of water soluble diluents include 1-octanol, 1-pentanol, 1-hexanol, 2-hexanol, 2-octanol, 3-methyl-3-pentanol, 2-pentanol, t-amyl alcohol, tert-butanol, 2-butanol, 1-butanol, 2-methyl-2-pentanol, 2-ethyl-1-butanol, ethanol, 3,3-dimethyl-2-butanol, decanoic acid, octanoic acid, dodecanoic acid, 1-ethoxy-2-propanol, 1-tert-butoxy-2-propanol, EH-5 (commercially available from Ethox Chemicals), 2,3,6,7-tetrahydroxy-2,3,6,7-tetramethyl octane, 9-(1-methylethyl)-2,5,8,10,13,16-hexaoxaheptadecane, 3,5,7,9,11,13-hexamethoxy-1-tetradecanol, mixtures thereof and the like.

The reactive mixture of the present invention may be cured via any known process for molding the reaction mixture in the production of contact lenses, including spincasting and static casting. Spincasting methods are disclosed in U.S. Pat. Nos. 3,408,429 and 3,660,545, and static casting methods are disclosed in U.S. Pat. Nos. 4,113,224 and 4,197,266. In one embodiment, the contact lenses of this invention are formed by the direct molding of the silicone hydrogels, which is economical, and enables precise control over the final shape of the hydrated lens. For this method, the reaction mixture is placed in a mold having the shape of the final desired silicone hydrogel, i.e. water-swollen polymer, and the reaction mixture is subjected to conditions whereby the monomers polymerize, to thereby produce a polymer in the approximate shape of the final desired product.

After curing the lens is subjected to extraction to remove unreacted components and release the lens from the lens mold. The extraction may be done using conventional extraction fluids, such as organic solvents, such as alcohols or may be extracted using aqueous solutions.

Aqueous solutions are solutions which comprise water. In one embodiment the aqueous solutions of the present invention comprise at least about 30% water, in some embodiments at least about 50% water, in some embodiments at least about 70% water and in others at least about 90 weight % water. Aqueous solutions may also include additional water soluble components such as the uncrosslinked statistical copolymers of the present invention, release agents, wetting agents, slip agents, pharmaceutical and nutraceutical components, combinations thereof and the like.

Pharmaceutical and nutraceutical components are known and include cationic drugs and neutriceuticals. Examples include those for the treatment of dry eye mitigation and/or prevention (including contact lens related dry eye, excessive tear evaporation and Non-Sjogren's aqueous tear deficiency), glaucoma, allergies (including antihistimines and mast cell inhibitors), ocular inflammation, ocular redness, ocular itching, bacterial, viral and fungal infections, prevention or slowing of myopia progression, and anaesthetics. Examples of cationic drugs include atropine, pirenzepine, doxycycline, brimonidine, brinzolamide, dorzolamide, betaxolol, apraclonidine, ccr2 antagonist, olopatadine, alcaftadine, betaxolol, bupivacaine, carbachol, carteolol, chlortetracycline, cyclopentolate, dibutoline, dipivefrin, ephedrine, erythromycin, gentamycin, gramicidin, homatropine ketotifen, levobunolol, levocabastine, lidocaine, lignocaine, lomefloxacin, mepivacaine, naphazoline, neomycin, ofloxacin, oxybuprocaine, pheniramine, physostigmine, pilocarpine, polymyxin B, proparacaine, pyrilamine, tetracaine, tetracycline, tetrahydozoline, timolol, tropicamide, vidarabine, pharmaceutically acceptable salts thereof and combinations thereof and the like. In another embodiment suitable pharmaceutical components include atropine, pirenzepine, doxycycline, brimonidine, brinzolamide, dorzolamide, betaxolol, apraclonidine, ccr2 antagonist, olopatadine, alcaftadine, betaxolol, bupivacaine, carbachol, carteolol, chlortetracycline, cyclopentolate, dibutoline, dipivefrin, erythromycin, gentamycin, gramicidin, homatropine ketotifen, levobunolol, levocabastine, lidocaine, lignocaine, lomefloxacin, mepivacaine, naphazoline, ofloxacin, pheniramine, physostigmine, pilocarpine, polymyxin B, proparacaine, pyrilamine, tetracaine, tetrahydozoline, timolol, tropicamide pharmaceutically acceptable salts thereof and combinations thereof and the like.

In another embodiment the cationic drugs include atropine, ketotifen, olopatadine, alcaftadine, levocabastine, pirenzepine, doxycycline, brimonidine, brinzolamide, dorzolamide, betaxolol, apraclonidine, ccr2 antagonist, olopatadine pharmaceutically acceptable salts thereof and combinations thereof and the like.

The drugs may be incorporated into the lenses in a symptom mitigating effective amount. Suitable amounts will vary for each drug, but include those between about the weight of the drug contained in an ophthalmic device prior to its use by a patient wherein such minimum effective amount alleviates the symptoms of the condition being treated. The minimum effective amount may vary depending upon the efficacy of a particular drug. General ranges include between about 5 µg and about less than 200 µg, and in some embodiments between about 9 µg and about less than 100 µg, with the symptom mitigating effective amount being selected to achieve the desired clinical result while minimizing undesired side effects.

For example, if the anti-allergic agent is ketotifen fumarate, the minimum effective amount is between greater than about 9 µg and about less than 90 µg, more particularly between about 40 µg and greater than about 9 µg, most preferably about 20 µg.

It is preferred that the minimum effective amount of drug alleviates the symptoms for between about 5 minutes, and about 24 hours from insertion of the ophthalmic device into the eye of a user, more preferably between about 5 minutes and about 16 hours, most preferably between about 5 minutes and about 12 hours.

The lenses of the present invention display surprisingly improved drug uptake compared to uncharged silicone hydrogel lenses and to anionic conventional lenses, such as etafilcon A. This is illustrated by the increase in uptake efficiency, uptake/[MAA], which was calculated using the following equation:

$$[(\text{Ketotifen uptake}_{ionic\ lens}/\text{Ketotifen uptake}_{non-ionic\ lens})/[MAA]_{ionic\ lens}] \times 100$$

Thus in one embodiment the lenses of the present invention display uptake efficiencies greater than about 200, greater than about 250, and in some embodiments, greater than about 300. While efficiency in the uptake of drug is increased, the uptake in polycationic ophthalmic solution component uptake, such as PQ1 uptake is maintained at a desirable level.

The ionic silicone hydrogel polymers of the present invention also display stable modulus. As used herein, stable modulus are those which increase less than about 30%, and in some embodiments less than about 20% over three autoclave cycles (20 minutes at 121° C.). In some embodiments the silicone hydrogel polymers of the present invention display modulus that increase by less than about 20% over 20 weeks over three autoclave cycles. In another embodiment, the ionic silicone hydrogels of the present invention display modulii which change less than about 30%, about 20% or even less than about 10% over 12 or 18 months at 25° C. and ambient humidity.

Still further the invention includes a method of making an ophthalmic device comprising about a minimum effective amount of an anti-allergic agent comprising the step of treating an ophthalmic device with a solution comprising said anti-allergic agent, wherein the amount of said anti-allergic agent in said solution exceeds the minimum effective amount. It is preferred that the minimum effective amount is exceeded by between about 1.0% and about 1000%, in a volume of solution that is between about 500 µL and about 5000 µL preferably between about 50% and about 500%, in a volume of solution that is between about 500 µL and about 3000 µL most preferably about 50% in a volume of solution that is about 1000 µL.

As used herein treating means physical methods of contacting the solution containing an anti-allergic agent and the ophthalmic device. Preferably treating refers to physical methods of contacting the anti-allergic agent with the ophthalmic devices prior to selling or otherwise delivering the ophthalmic devices to a patient. The ophthalmic devices may be treated with the anti-allergic agent anytime after they are polymerized.

Release agents are compounds or mixtures of compounds which, when combined with water, decrease the time required to release a contact lens from a mold, as compared to the time required to release such a lens using an aqueous solution that does not comprise the release agent. In one embodiment the aqueous solutions comprise less than about 10 weight %, and in others less than about 5 weight % organic solvents such as isopropyl alcohol, and in another embodiment are free from organic solvents. In these embodiments the aqueous solutions do not require special handling, such as purification, recycling or special disposal procedures.

In various embodiments, extraction can be accomplished, for example, via immersion of the lens in an aqueous solution or exposing the lens to a flow of an aqueous solution. In various embodiments, extraction can also include, for example, one or more of: heating the aqueous solution; stirring the aqueous solution; increasing the level of release aid in the aqueous solution to a level sufficient to cause release of the lens; mechanical or ultrasonic agitation of the lens; and incorporating at least one leach aid in the aqueous solution to a level sufficient to facilitate adequate removal of unreacted components from the lens. The foregoing may be conducted in batch or continuous processes, with or without the addition of heat, agitation or both.

Some embodiments can also include the application of physical agitation to facilitate leach and release. For example, the lens mold part to which a lens is adhered, can be vibrated or caused to move back and forth within an aqueous solution. Other embodiments may include ultrasonic waves through the aqueous solution.

These and other similar processes can provide an acceptable means of releasing the lens.

As used herein, "released from a mold" means that a lens is either completely separated from the mold, or is only loosely attached so that it can be removed with mild agitation or pushed off with a swab. In the process of the present invention the conditions used include temperature less than 99° C. for less than about 1 hour.

The lenses may be sterilized by known means such as, but not limited to autoclaving. The uncrosslinked, statistical copolymers may be added before or after polymerization.

In one embodiment, ophthalmic devices formed from the polymers of the present invention display excellent compatibility with the components of human tears.

Human tears are complex and contain a mixture of proteins, lipids and other components which help to keep the eye lubricated. Examples of proteins which are found in human tears include lactoferrin, lysozyme, lipocalin, serum albumin, and secretory immunoglobulin A.

Lysozyme is generally present in human tears in substantial concentrations. Lysozyme is bacteriolytic and believed to protect the eye against bacterial infection. The amount of lysozyme which associates with commercially available contact lenses when worn, varies greatly from only a few micrograms to over 800 micrograms for etafilcon A contact lenses (commercially available from Johnson & Johnson Vision Care, Inc., under the ACUVUE and ACUVUE2 brand names). Etafilcon A contact lenses have been commercially available for many years and display some of the lowest adverse event rates of any soft contact lens. Thus, contact lenses which uptake substantial levels of lysozyme are desirable. The lenses of the present invention uptake at least about 50 µg, 100 µg, 200 µg, 500 µg of lysozyme and in some embodiments at least about 800 µg lysozyme, all from a 2 mg/ml solution over 72 hours incubation at 35° C. In another embodiment the silicone hydrogels of the present invention display both desirable lysozyme uptake and water content. Desirable water contents are those between about 20 and about 70%, between about 25 and about 70%, and in some embodiments between about 25 and about 65 wt %. The foregoing ranges may be combined in any variation.

In addition to lysozyme, lactoferrin is another important cationic protein in the tears, mainly by the virtue of its anti-bacterial and anti-inflammatory properties. Upon wear, contact lenses uptake various amounts of lactoferrin, depending upon their polymer composition (for non-surface modified lenses) and the composition and integrity of the surface coating (for surface modified contact lenses). In one embodiment of the present invention, lenses uptake at least about 5 µg, and in some embodiments, at least about 10 micrograms lactoferrin following overnight soaking of the lenses in 2 mls of a 2 mg/ml lactoferrin solution. The lactoferrin solution contains lactoferrin from human milk (Sigma L-0520) solubilized at a concentration of 2 mg/ml in phosphate saline buffer. Lenses are incubated in 2 ml of the lactoferrin solution per lens for 72 hours at 35° C., using the procedure described below for lysozyme. Lactoferrin and lysozyme also act synergistically as bactericidal agents.

The form of the proteins in, on and associated with the lens is also important. Denatured proteins are believed to contribute to corneal inflammatory events and wearer discomfort. Environmental factors such as pH, ocular surface temperature, wear time and closed eye wear are believed to contribute to the denaturation of proteins. However, lenses of different compositions can display markedly different protein uptake and denaturation profiles. In one embodiment of the present invention, a majority of the proteins uptaken by the lenses of the present invention are and remain in the native form during wear. In other embodiments at least about 50%, at least about 70 and at least about 80% of uptaken proteins are and remain native after 24 hours, 3 days and during the intended wear period.

In one embodiment the ophthalmic devices of the present invention also uptake less than about 20%, in some embodiments less than about 10%, and in other embodiments less than about 5% Polyquaternium-1 ("PQ1") from an ophthalmic solution containing 0.001 wt % PQ1 and citrate dihydrate and citric acid monohydrate.

The lenses of the present invention have a number of desirable properties in addition to the protein uptake characteristics described herein. In one embodiment the lenses have an oxygen permeability greater than about 50 and in other embodiments greater than about 60, in other embodiments greater than about 80 and in still other embodiments at least about 100. In some embodiments the lenses have tensile moduli less than about 100 psi.

The biomedical devices, and particularly ophthalmic lenses of the present invention have a balance of properties which makes them particularly useful. Such properties include clarity, water content, oxygen permeability and contact angle. Silicone hydrogel contact lenses formed from the polymers of the present invention display contact angles of less than about 70°, less than about 50° and in some embodiments less than about 30° all as measured by sessile drop, and decreases in contact angle of about 30% and in some embodiments about 50% or more.

In one embodiment, the biomedical devices are contact lenses having a water content of greater than about 20% and more preferably greater than about 25%.

As used herein clarity means substantially free from visible haze. Preferably clear lenses have a haze value of less than about 150%, more preferably less than about 100%.

Suitable oxygen permeabilities for silicone containing lenses are preferably greater than about 40 barrer and more preferably greater than about 60 barrer.

In some embodiments the articles of the present invention have combinations of the above described oxygen permeability, water content and contact angle. All combinations of the above ranges are deemed to be within the present invention.

It will be appreciated that all of the tests specified herein have a certain amount of inherent test error. Accordingly, results reported herein are not to be taken as absolute numbers, but numerical ranges based upon the precision of the particular test.

Wettability of lenses was determined using a sessile drop technique measured using KRUSS DSA-100™ instrument at room temperature and using DI water as probe solution. The lenses to be tested (3-5/sample) were rinsed in DI water to remove carry over from packing solution. Each test lens was placed on blotting lint free wipes which were dampened with packing solution. Both sides of the lens were contacted with the wipe to remove surface water without drying the lens. To ensure proper flattening, lenses were placed "bowl side down" on the convex surface on contact lens plastic moulds. The plastic mould and the lens were placed in the sessile drop instrument holder, ensuring proper central syringe alignment and that the syringe corresponds to the assigned liquid. A 3 to 4 microliter of DI water drop was formed on the syringe tip using DSA 100-Drop Shape Analysis software ensuring the liquid drop was hanging away from the lens. The drop was released smoothly on the lens surface by moving the needle down. The needle was withdrawn away immediately after dispensing the drop. The liquid drop was allowed to equilibrate on the lens for 5 to 10 seconds and the contact angle was measured between the drop image and the lens surface.

The water content may be measured as follows: lenses to be tested were allowed to sit in packing solution for 24 hours. Each of three test lens were removed from packing solution using a sponge tipped swab and placed on blotting wipes which have been dampened with packing solution. Both sides of the lens were contacted with the wipe. Using tweezers, the test lens were placed in a weighing pan and weighed. The two more sets of samples were prepared and weighed as above. The pan was weighed three times and the average is the wet weight.

The dry weight was measured by placing the sample pans in a vacuum oven which has been preheated to 60° C. for 30 minutes. Vacuum was applied until at least 0.4 inches Hg is attained. The vacuum valve and pump were turned off and the lenses were dried for four hours. The purge valve was opened and the oven was allowed reach atmospheric pressure. The pans were removed and weighed. The water content was calculated as follows:

Wet weight =
 combined wet weight of pan and lenses − weight of weighing pan

Dry weight = combined dry weight of pan and lens −
 weight of weighing pan $$\% \text{ water content} = \frac{(\text{wet weight} - \text{dry weight})}{\text{wet weight}} \times 100$$

The average and standard deviation of the water content are calculated for the samples are reported.

Haze may measured by placing a hydrated test lens in borate buffered saline in a clear 20×40×10 mm glass cell at ambient temperature above a flat black background, illuminating from below with a fiber optic lamp (Titan Tool Supply Co. fiber optic light with 0.5" diameter light guide set at a power setting of 4-5.4) at an angle 66° normal to the lens cell, and capturing an image of the lens from above, normal to the lens cell with a video camera (DVC 1300C:19130 RGB camera with Navitar TV Zoom 7000 zoom lens) placed 14 mm above the lens platform. The background scatter is subtracted from the scatter of the lens by subtracting an image of a blank cell using EPIX XCAP V 1.0 software. The subtracted scattered light image is quantitatively analyzed, by integrating over the central 10 mm of the lens, and then comparing to a −1.00 diopter CSI Thin Lens®, which is arbitrarily set at a haze value of 100, with no lens set as a haze value of 0. Five lenses are analyzed and the results are averaged to generate a haze value as a percentage of the standard CSI lens.

Oxygen permeability (Dk) may be determined by the polarographic method generally described in ISO 9913-1: 1996(E), but with the following variations. The measurement is conducted at an environment containing 2.1% oxygen. This environment is created by equipping the test chamber with nitrogen and air inputs set at the appropriate ratio, for example 1800 ml/min of nitrogen and 200 ml/min of air. The t/Dk is calculated using the adjusted $p_{O2}$. Borate buffered saline was used. The dark current was measured by using a pure humidified nitrogen environment instead of applying MMA lenses. The lenses were not blotted before measuring. Four lenses were stacked instead of using lenses of varied thickness. A curved sensor was used in place of a flat sensor. The resulting Dk value is reported in barrers.

Lysozyme uptake was measured as follows: The lysozyme solution used for the lysozyme uptake testing contained lysozyme from chicken egg white (Sigma, L7651) solubilized at a concentration of 2 mg/ml in phosphate saline buffer supplemented by Sodium bicarbonate at 1.37 g/l and D-Glucose at 0.1 g/l.

Three lenses for each example were tested using each protein solution, and three were tested using PBS as a control solution. The test lenses were blotted on sterile gauze to remove packing solution and aseptically transferred, using sterile forceps, into sterile, 24 well cell culture plates (one lens per well) each well containing 2 ml of lysozyme solution. Each lens was fully immersed in the solution. 2 ml of the lysozyme solution was placed in a well without a contact lens as a control.

The plates containing the lenses and the control plates containing only protein solution and the lenses in the PBS, were sealed using parafilm to prevent evaporation and dehydration, placed onto an orbital shaker and incubated at 35° C., with agitation at 100 rpm for 72 hours. After the 72 hour incubation period the lenses were rinsed 3 to 5 times by dipping lenses into three (3) separate vials containing approximately 200 ml volume of PBS. The lenses were blotted on a paper towel to remove excess PBS solution and transferred into sterile conical tubes (1 lens per tube), each tube containing a volume of PBS determined based upon an estimate of lysozyme uptake expected based upon on each lens composition. The lysozyme concentration in each tube to be tested needs to be within the albumin standards range as described by the manufacturer (0.05 micogram to 30 micrograms). Samples known to uptake a level of lysozyme lower than 100 µg per lens were diluted 5 times. Samples known to uptake levels of lysozyme higher than 500 µg per lens (such as etafilcon A lenses) are diluted 20 times.

1 ml aliquot of PBS was used for all samples other than etafilcon. 20 ml were used for etafilcon A lens. Each control lens was identically processed, except that the well plates contained PBS instead of lysozyme solution.

Lysozyme uptake was determined using on-lens bicinchoninic acid method using QP-BCA kit (Sigma, QP-BCA) following the procedure described by the manufacturer (the standards prep is described in the kit) and is calculated by subtracting the optical density measured on PBS soaked lenses (background) from the optical density determined on lenses soaked in lysozyme solution.

Optical density was measured using a SynergyII Microplate reader capable for reading optical density at 562 nm.

PQ-1 Uptake

PQ1 uptake was measured as follows: The HPLC is calibrated using a series of standard PQ1 solutions prepared having the following concentrations: 2, 4, 6, 8, 12 and 15 µg/mL. Lenses were placed into polypropylene contact lens case with 3 mL of Optifree Replenish (which contains 0.001 wt % PQ1, 0.56% citrate dihydrate and 0.021% citric acid monohydrate (wt/wt)) and is commercially available from Alcon). A control lens case, containing 3 mL of solution, but no contact lens was also prepared. The lenses and control solutions were allowed to sit at room temperature for 72 hours. 1 ml of solution was removed from each of the samples and controls and mixed with trifluoroacetic acid (10 µL). The analysis was conducted using HPLC/ELSD and a Phenomenex Luna C4 (4.6 mm×5 mm; 5 µm particle size) column and the following conditions:

Instrument: Agilent 1200 HPLC or Equivalent with Sedere Sedex 85 ELSD

Sedex 85 ELSD: T=60° C., Gain=10, Pressure=3.4 bar, Filter=1s

Mobile Phase A: $H_2O$ (0.1% TFA)

Mobile Phase B: Acetonitrile (0.1% TFA)

Column Temperature: 40° C.

Injection Volume: 100 µL

TABLE I

| Time (minutes) | % A | % B | Flow Rate (mL/min) |
|---|---|---|---|
| 0.00 | 100 | 0 | 1.2 |
| 1.00 | 100 | 0 | 1.2 |
| 5.00 | 0 | 100 | 1.2 |
| 8.50 | 0 | 100 | 1.2 |
| 8.60 | 100 | 0 | 1.2 |
| 12.00 | 100 | 0 | 1.2 |

Three lenses were run for each analysis, and the results were averaged.

The non-limiting examples below further describe this invention.

| | |
|---|---|
| ACA1 | 3-acrylamidopropanoic acid |
| ACA2 | 5-acrylamidopentanoic acid |
| AMPS | 2-Acrylamido-2-methylpropane sulfonic acid, CAS 15214-89-8 |
| Bis HEAA | N,N bis-(2-hydroxyethyl)acrylamide |
| Blue Hema | the reaction product of Reactive Blue 4 and HEMA, as described in Example 4 of U.S. Pat. No. 5,944,853 |
| DMA | N,N dimethyl acrylamide (Jarchem) |
| D3O | 3,7-dimethyl-3-octanol |
| Norbloc | 2-(2'-hydroxy-5-methacrylyloxyethylphenyl)-2H-benzotriazole |
| Irgacure 819 | bis(2,4,6-trimethylbenzoyl)-phenylphosphineoxide |
| MAA | methacrylic acid |
| MBA | N,N'-Methylene-bisacrylamide (Sigma-Aldrich) |
| PVP | polyvinyl pyrrolidone (K90) |
| HO-mPDMS | mono-(2-hydroxy-3-methacryloxypropyl)-propyl ether terminated, n-butyl terminated polydimethylsiloxane (400-1000 MW)) |
| SA2 | N-(2,3-dihydroxypropane)-N'-(propyl tetra(dimethylsiloxy) dimethylbutylsilane)acrylamide, made by working example 2 and shown in Formula 8 of US2011/0237766 |
| PQ1 | poly[(dimethyliminio)-2-butene-1,4-diyl chloride (1:1)], α-[4-[tris(2-hydroxyethyl)ammonio]-2-buten-1-yl-ω-[tris(2-hydroxyethyl)ammonio]-, chloride (CAS 75345-27-6) |

Synthesis 1

S-hexyl-S-4-(2-(n-butylpolydimethylsiloxysilyl) ethyl)benzyl carbonotrithioate

XG-1996 (shown in Formula I, MW distribution centered around about 1000 g/mole, which corresponds to an average repeat, m of 10-12), (10 g, 10 moles), Formula I

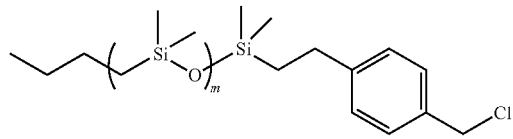

XG-1996: Chloromethylphenylethylpolydimethylsiloxane MW~1000 g/mole was dissolved in approx. 250 mL of acetone in a 1 L round bottom flask. Sodium hexyltrithiocarbonate (NaHTTC) was dissolved in 100 mL acetone and added to the reaction mixture. The reaction mixture was stirred overnight. A white solid precipitated out of the bright yellow solution. Acetone was removed via rotary-evaporation, and the crude product was partitioned between 250 mL DI water and 250 mL hexane. The hexane layer was separated out and the aqueous layer was extracted with hexane (3×200 mL). All organic layers were combined, washed with brine (250 mL) and dried over $Na_2SO_4$. The crude product in hexane was passed over a silica gel plug to remove cloudiness. Hexane was removed via rotary-evaporation leaving the product (XG-1996-HTTC) in the form of a clear yellow oil. Structure was confirmed using NMR spectroscopy.

Synthesis 2: 3-acrylamidopropanoic acid

A fresh solution of sodium methoxide was prepared by dissolving 4.6 g of metallic sodium in 250 mL of stirred methanol, to which, Beta-alanine (3-aminopentanoic acid, 8.9 g, 0.1 mole) was added.

Acryloyl chloride (10.0 g, 1.1 eq.) was added dropwise to a stirred suspension of the given mixture, while maintaining the temperature below 35 C at all times. The mixture was stirred for an additional 30 minutes, concentrated to about 50 mL and filtered to remove the sodium chloride formed. The hygroscopic product was treated with pH 3 aqueous HCl, followed by evaporation of the volatiles ad filtration through silica gel using 3-5% (v/v) methanol in ethyl acetate.

Synthesis 3: 5-Acrylamidopentanoic acid (ACA II)

A fresh solution of sodium methoxide was prepared by dissolving 5.76 g of metallic sodium in 250 mL of stirred methanol. Valeric acid (5-aminopentanoic acid, 14.68 g, 0.125 mole) was dissolved in the given solution and 2.1 g of sodium carbonate was added to the mixture.

Acryloyl chloride (12.31 g, 1.1 eq.) was added dropwise to a stirred suspension of the given mixture, while maintaining the temperature below 35 C at all times. The mixture was stirred for an additional 30 minutes and filtered to remove the sodium chloride and residual carbonate present.

Evaporation of the methanol and other volatiles at reduced pressure, followed by washing the residue with 2×75 mL of acetonitrile yielded 20.4 g of the sodium salt of 5-acrylamidopentanoic acid. The free carboxylic acid was obtained pure after acidification of the salt in pH 3 aqueous HCl, evaporation of the residual water, followed by filtration through silica gel using 2-3% (v/v) methanol in ethyl acetate.

Preparation 1

N,N-dimethylacrylamide (DMA) and further purified via vacuum distillation. 5-acrylamidopentanoic acid (ACA2) was prepared according to Synthesis 3 The siloxy-functional benzyltrithiocarbonate, S-XG-1996-S'-hexyl-trithiocarbonate, was prepared according to Synthesis 1, above. Irgacure 819 was dissolved in D3O (10 mg/mL).

The polymerization solution was prepared by dissolving 1.1 g ACA2 in 3 mL of ethanol and 1.5 g DMA in an amber 20 mL glass vial. Next, 166 mg S-XG-1996-S'-hexyl-trithiocarbonate, and 1.51 mg (151 ul of stock solution) Irgacure-819 were added to the monomer and warmed/stirred to ensure homogeneity (CTA to initiator ratio=20). The amber vial containing the final polymerization solution was sealed with a rubber septum and purged for 20 minutes with $N_2$ to remove $O_2$ from the solution. Finally the sealed jar was placed in an $N_2$ glove-box for storage.

The polymerization solution was cured under an $N_2$ atmosphere with 4 standard Phillips TL 20 W/03 RS bulbs at intensity of 2.0 $mW/cm^2$ for 45 minutes. Prior to curing, the polymerization solution was poured into an 80 mm diameter crystallization dish, which was then placed on a reflective glass surface.

After curing, the resulting highly viscous polymerized material was dissolved in 5 mL of ethanol. The solution was stirred then added drop-wise to vigorously stirring diethyl ether to precipitate product. A 500 mL flask filled with 200 mL of ether was used. The precipitated polymer was dried in vacuo for several hours. The polymer was analyzed for MW and MWD via SEC-MALLS. The degree of polymerization of the hydrophilic segment was about 300.

The reaction is shown below.

placed in an $N_2$ glove-box for storage. The polymerization solution was cured and purified as described in Preparation 1. The polymer was analyzed for MW and MWD via SEC-MALLS. The degree of polymerization of the hydrophilic segment was about 300.

Preparations 3 and 4 (PDMA/ACA2 Copolymer, Dp=300)

N,N-dimethylacrylamide (DMA) was obtained from Jarchem and further purified via vacuum distillation. S-benzyl-S'-hexyl-trithiocarbonate was prepared according to Synthesis 1. Irgacure 819 (1.06 mg) was dissolved in D3O (10 mg/mL).

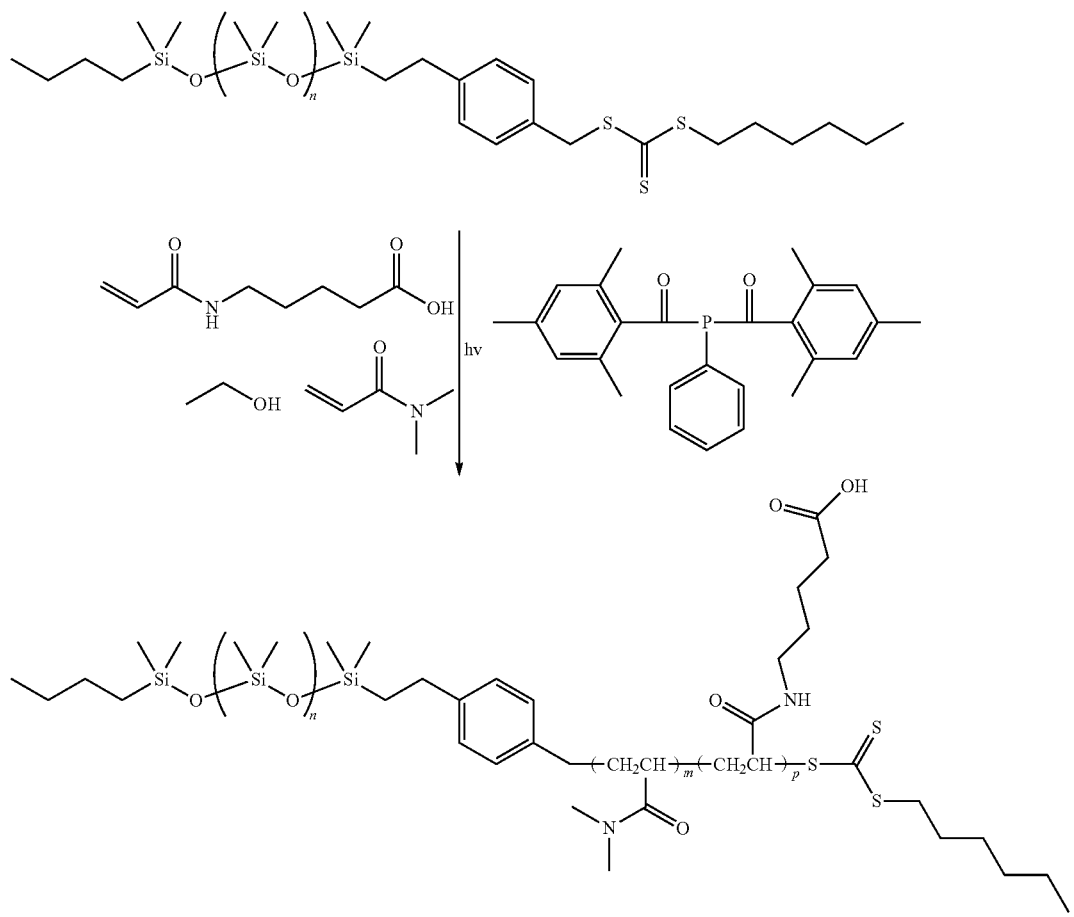

Preparation 2

N,N-dimethylacrylamide (DMA) was purified via vacuum distillation. 5-acrylamidopentanoic acid (ACA2) was prepared according to Synthesis 3. The siloxy-functional benzyltrithiocarbonate, S-XG-1996-S'-hexyl-trithiocarbonate, was prepared according to Synthesis 1. Irgacure 819, was obtained from Ciba Specialty Chemicals and dissolved in D3O (10 mg/mL).

The polymerization solution was prepared by dissolving 2.07 g ACA2 in 6 mL ethanol and 300 mg DMA in an amber 20 mL glass vial. Next, 58 mg S-XG-1996-S'-hexyl-trithiocarbonate, and 1.06 mg (106 ul of stock solution) Irgacure-819 were added to the monomer and warmed/stirred to ensure homogeneity (CTA to initiator ratio=20). The amber vial containing the final polymerization solution was sealed with a rubber septum and purged for 20 minutes with $N_2$ to remove $O_2$ from the solution. Finally the sealed vial was

TABLE 2

| Materials | Prep 3<br>80 DMA/20ACA2 | Prep 4<br>70 DMA/30ACA2 |
|---|---|---|
| CTA | 14 mg | 20 mg |
| Ethanol | 6 Ml | 3 mL |
| DMA | 300 mg | 1.5 g |
| ACA II | 2.07 g | 1.1 g |
| Irgacure-819 | 1.06 mg | 1.51 mg |

The polymerization solution was prepared by dissolving the ACA2 in ethanol and DMA in an amber 20 mL glass vial. Next, S-benzyl-S'-hexyl-trithiocarbonate, and (1.51 ul of stock solution) Irgacure-819 were added to the monomer and warmed/stirred to ensure homogeneity (CTA to initiator ratio=20). The amounts for each component are shown in Table 2, above. The amber vial containing the final polymerization solution was sealed with a rubber septum and purged for 20 minutes with $N_2$ to remove $O_2$ from the solution. Finally the sealed jar was placed in an $N_2$ glovebox for storage.

The polymerization solution was cured under an $N_2$ atmosphere with 4 standard Phillips TL 20 W/03 RS bulbs at intensity of 2.0 mW/cm² for 45 minutes. Prior to curing, the polymerization solution was poured into an 80 mm diameter crystallization dish, which was then placed on a reflective glass surface.

The resulting polymerized material was dissolved in 5 mL of ethanol. The solution was stirred then added drop-wise to vigorously stirring diethyl ether to precipitate product. A 500 mL flask filled with 200 mL of ether was used. The precipitated polymer was dried in vacuo for several hours. The polymer was analyzed for MW and MWD via SEC-MALLS. The reaction is shown below.

sured and are reported in Table 3. Untreated senofilcon lenses were also tested as a control.

TABLE 3

| Ex# | Prep | DMA:ionic | [NRPTHP] (ppm) | CA° | % PQ1 uptake | Lysozyme (µg/lens) |
|---|---|---|---|---|---|---|
| 1 | 1 | 70:30ACA2 | 50 | 24 ± 5 | 7 ± 1 | 19 ± 3 |
| 2 | 1 | 70:30ACA2 | 500 | 28 ± 6 | 0 ± 0 | 44 ± 7 |
| 3 | 1 | 70:30ACA2 | 1000 | 29 ± 7 | 0 ± 5 | 51 ± 6 |
| 4 | 2 | 80:20ACA2 | 50 | 24 ± 13 | 9 ± 0 | 33 ± 5 |
| 5 | 2 | 80:20ACA2 | 500 | 32 ± 18 | 24 ± 9 | 58 ± 7 |
| 6 | 2 | 80:20ACA2 | 1000 | 33 ± 16 | 46 ± 7 | 65 ± 4 |
| 7 | 3 | 80:20ACA2 | 50 | 17 ± 4 | 7 ± 5 | 23 ± 4 |
| 8 | 3 | 80:20ACA2 | 500 | 22 ± 12 | 13 ± 1 | 43 ± 5 |
| 9 | 3 | 80:20ACA2 | 1000 | 21 ± 6 | 5 ± 6 | 42 ± 2 |
| 10 | 4 | 70:30ACA2 | 50 | 30 ± 15 | 1 ± 0 | 23 ± 2 |
| 11 | 4 | 70:30ACA2 | 500 | 21 ± 19 | 24 ± 13 | 65 ± 3 |
| 12 | 4 | 70:30ACA2 | 1000 | 37 ± 20 | 25 ± 13 | 66 ± 5 |

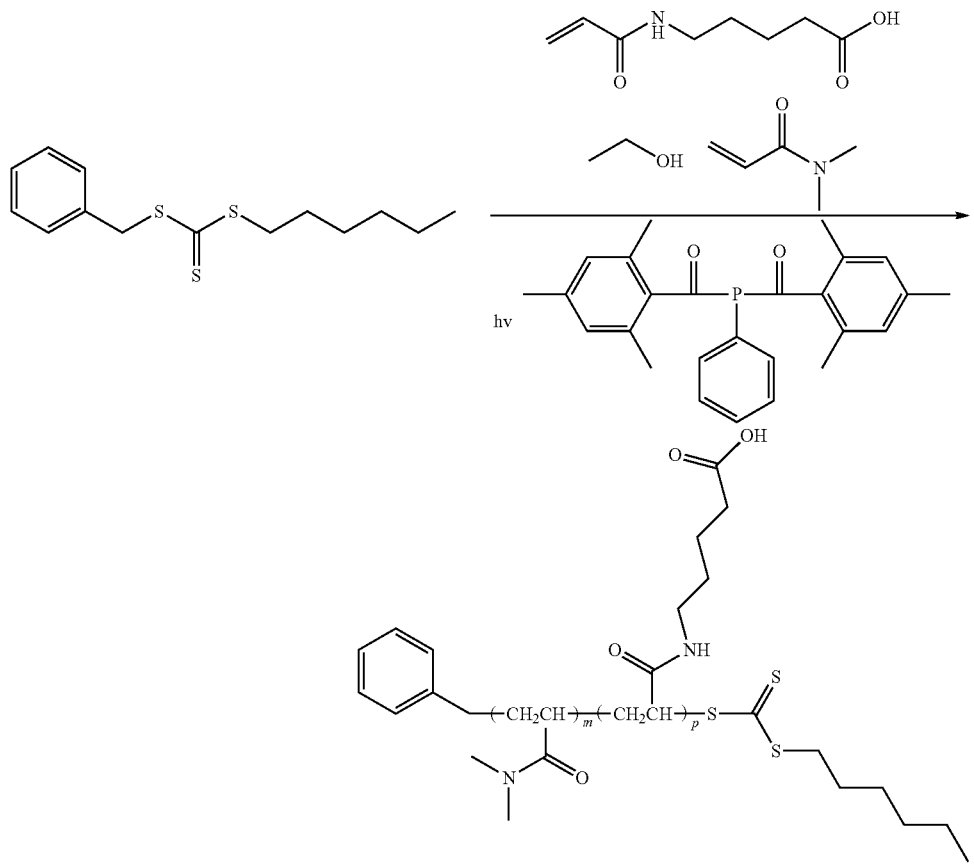

Examples 1-12

Three senofilcon lenses were removed from their packages and transferred glass vials containing packing solution containing the non-reactive polysiloxane terminated hydrophilic polymer ("NRPTHP") produced in Preparation 1 through 4 in the concentrations shown in Table 1. The lenses were re-packaged in the NRPTHP packing solution, autoclaved at 121° C. for 28 minutes and, after sterilization, were allowed to soak in the NRPTHP packing solution at ambient temperature for at least 24 hours. The contact angle, lysozyme uptake and PQ-1 uptake of the lenses were mea- TABLE 3-continued

| Ex# | Prep | DMA:ionic | [NRPTHP] (ppm) | CA° | % PQ1 uptake | Lysozyme (µg/lens) |
|---|---|---|---|---|---|---|
| CE1 | 5 | 70:30AA | 500 | NM | 19 + 5 | 31 + 7 |
| CE2 | 6 | 20:80AA | 500 | NM | 65 + 21 | 65 + 5 |
| CE3 | 7 | 70:30AA | 500 | NM | 10 + 2 | 26 + 3 |
| CE4 | 8 | 20:80AA | 500 | NM | 45 ± 9 | 73 + 4 |

The data in Table 3 shows that non-reactive hydrophilic copolymers comprising a randomly copolymerized anionic monomer are effective at reducing contact angle. The hydrophilic copolymer of Preparations 1 and 2 contained an anionic component, APA which in the concentrations of Examples 2 through 4 were effective in increasing lysozyme uptake to at least about 50 μg/lens and decreasing PQ1 uptake. Lysozyme is a protein native to the eye which, when uptaken in a contact lens in the native form, is believed to improve the biocompatibility of the contact lens. PQ1 is a preservative commonly used in contact lens multipurpose solutions. Uptake of PQ1 to a contact lens in amounts greater than about 10% can cause staining and is therefore undesirable. Examples 1-12 display lower values of PQ1 uptake compared to the lenses treated with acrylic acid containing polymers of Comparative Examples 1-4. The lenses of Examples 2-4 and 9 display a desirable balance of contact angle, lysozyme and PQ1 uptake.

Preparation Examples 5 and 6

DMA was purified via vacuum distillation. Acrylic acid (Sigma Aldrich) was used as received. S-XG-1996-S'-hexyl-trithiocarbonate, was prepared according to Synthesis 1. Irgacure 819, was dissolved in decanol (10 mg/mL).

TABLE 3a

| Materials | [CE5-30%] (gm) | [CE6-80%] (gm) |
|---|---|---|
| CTA | 0.553 | 0.508 |
| Pentanol | 13.0 | 11.0 |
| DMA | 10.0 | 3.00 |
| Acrylic Acid | 3.12 | 8.73 |
| Irgacure-819 | 0.00201 | 0.00211 |

The polymerization solution was prepared by adding distilled DMA and acrylic acid to an amber 30 mL glass jar. Next, pentanol, S-XG-1996-S'-hexyl-trithiocarbonate, and Irgacure-819 stock solution were added to the monomer in the amounts in Table 3a and warmed/stirred to ensure homogeneity (CTA to initiator ratio=100). The amber jar containing the final polymerization solution was sealed with a rubber septum and purged for 20 minutes with $N_2$ to remove $O_2$ from the solution. Finally the sealed jar was placed in an $N_2$ glove-box for overnight storage.

The polymerization solution was cured under an $N_2$ atmosphere with 4 standard Phillips TL 20 W/03 RS bulbs at intensity of 2.0 mW/cm² for 1 hour. Prior to curing, the polymerization solution was poured into a 125 mm diameter crystallization dish, which was then placed on a reflective glass surface.

After curing for 1 hour, the resulting highly viscous polymerized material was dissolved in 30 mL of ethanol. The solution was stirred overnight then transferred to an addition funnel using 20 mL of ethanol to rinse out the crystallization dish. The polymer solution was added drop-wise to vigorously stirring diethyl ether to precipitate product. A 1 L flask filled with 500 mL of ether was used. The precipitated polymer was dried in vacuo for several hours and then subjected to further purification via Soxhlet Extraction with diethyl ether. The polymer was analyzed for MW and MWD via SEC-MALLS.

Synthesis 4: Synthesis of Sodium Hexyltrithiocarbonate

The amount of reactants are shown in Table 3b.

TABLE 3b

| Materials | MW | Mass (g) | Moles | Equivalents |
|---|---|---|---|---|
| Sodium Metal | 23.0 | 9.74 | 0.423 | 1.0 |
| 1-Hexanethiol | 118.2 | 50.0 | 0.423 | 1.0 |
| Carbon Disulfide | 76.1 | 48.3 | 0.635 | 1.5 |

Sodium in kerosene (Sigma Aldrich) was weighed and submerged in a small beaker of hexane. It was added to 100 mL of methanol stirring in a 125 mL flask under nitrogen in several chunks over approximately 3 hours. Methanol was added to replace evaporated solvent. Sodium methoxide solution was slowly added via addition funnel to a 500 mL round bottom flask containing 1-hexanthiol (Sigma Aldrich) stirring in 50 mL methanol. The flask was placed in a cold water bath, and carbon disulfide (Sigma Aldrich) was added slowly via syringe. The reaction mixture immediately turned yellow and evolved heat. The mixture was stirred for approximately 15 minutes then evaporated to dryness under reduced pressure. Product is a bright yellow solid. The reaction is shown below:

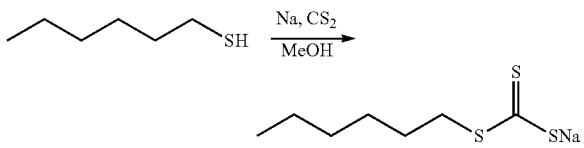

Synthesis 5: Synthesis of S-benzyl-S'-hexyl-trithiocarbonate

The amount of reactants are shown in Table 3c.

TABLE 3c

| Materials | MW | Mass (g) | Moles | Equivalents |
|---|---|---|---|---|
| Sodium Metal | 23.0 | 1.00 | 0.0435 | 1.0 |
| 1-Hexanethiol | 118.2 | 5.14 | 0.0435 | 1.0 |
| Carbon Disulfide | 76.1 | 3.64 | 0.04785 | 1.1 |
| Benzyl Bromide | 171.0 | 7.44 | 0.0435 | 1.0 |

Sodium in kerosene (Sigma Aldrich) was added in pieces slowly under nitrogen to 20 mL of methanol to form sodium methoxide. This solution was added to a flask containing 1-hexanethiol (Sigma Aldrich) in several aliquots. Carbon disulfide (Sigma Aldrich) was added drop-wise via syringe. The solution turned yellow immediately. The solution was allowed to react for 15 minutes. Benzyl bromide (Sigma Aldrich) was then added dropwise via syringe. A precipitate formed immediately. The reaction was allowed to proceed for two hours. A yellow oil eventually formed at the bottom of the flask. The methanol was roto-vapped off and the product was separated from the sodium salt with deionized water and hexane. The aqueous layer was approximately 50 mL and was extracted three times with 50 mL of hexane. The hexane was combined, dried over Na2SO4 and evaporated to dryness under pressure. The reaction is shown below.

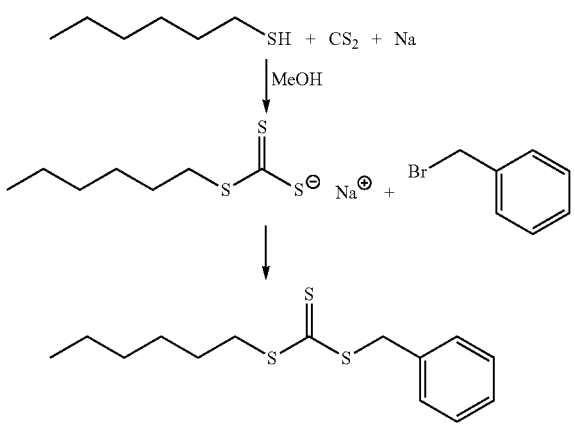

Preparations 7-8: Preparation of PDMA Acrylic Acid

DMA was purified via vacuum distillation. Acrylic acid (Sigma Aldrich) was used as received. S-benzyl-S'-hexyl-trithiocarbonate was prepared according to Procedure 1. Irgacure 819 was dissolved in decanol (10 mg/mL). The components were used in the amounts shown in Table 3d, below.

TABLE 3d

| Materials | P7-30% (g) | P8-80% (g) |
|---|---|---|
| CTA | 0.137 | 0.144 |
| Ethanol | 13.0 | 11.0 |
| DMA | 10.00 | 3.00 |
| Acrylic Acid | 3.12 | 8.73 |
| Irgacure-819 | 0.00201 | 0.00211 |

The polymerization solutions were prepared for each of Preparation 5-7 by adding DMA and acrylic acid to an amber 30 mL glass jar. Next, ethanol, S-benzyl-S'-hexyl-trithiocarbonate (CTA), and Irgacure-819 were added to the monomer and warmed/stirred to ensure homogeneity (CTA to initiator ratio=100). The amber jar containing the final polymerization solution was sealed with a rubber septum and purged for 20 minutes with $N_2$ to remove $O_2$ from the solution. Finally the sealed jar was placed in an $N_2$ glove-box for storage.

The polymerization solution was cured under an $N_2$ atmosphere with 4 standard Phillips TL 20 W/03 RS bulbs at intensity of 2.0 mW/cm². Prior to curing, the polymerization solution was poured into a 125 mm diameter crystallization dish, which was then placed on a reflective glass surface. No increase in viscosity was observed after 40 minutes under light. In each example another dose of Irgacur 819 equal to the initial dose was added to the dish lowering the CTA to initiator ratio to 50 to improve polymerization. The solution was mixed with swirling then exposed to light for another 30 minutes and became extremely viscous.

After curing, the resulting polymerized material was dissolved in 40 mL of ethanol. The solution was stirred overnight then transferred to an addition funnel using 20 mL of ethanol to rinse out the crystallization dish. The polymer solution was added drop-wise to vigorously stirring diethyl ether to precipitate product. A 1 L flask filled with 800 mL of ether was used. The precipitated polymer was dried in vacuo for several hours and then subjected to further purification via Soxhlet Extraction with diethyl ether. The polymers were analyzed for MW and MWD via SEC-MALLS.

Examples 13-15

A base reactive mixture having the components listed in Table 4, below was made by mixing the components in the amounts listed with t-amyl alcohol (55 wt % components:45 wt % t-amyl alcohol).

TABLE 4

| Component | Wt % |
|---|---|
| DMA | 29.45 |
| Blue HEMA | 0.02 |
| Norbloc 7966 | 2.2 |
| Irgacure 819 | 0.25 |
| MBA | 1.10 |
| SA2 | 55.98 |
| PVP K90 | 8.00 |
| Bis-HEAA | 3.00 |

Separate formulations were made adding 3 mol % of the ionic component listed in Table 5, below. The formulations were stirred on a jar roller for 2 hours, and then filtered. Each reactive mixture was degassed, dosed into molds (Zeonor FC/polypropylene BC) and cured for 5 minutes, at about 55° C., about 2.25 mW/cm² intensity, and about 0.2% $O_2$. The molds were separated by hand. The lenses were released and extracted in 70/30 IPA/DI and finally hydrated in standard packing solution. The lenses were sterilized at 121° C. for 20 minutes. The sterilized lenses were tested for lysozyme and PQ1 uptake.

Comparative Example 5 were lenses made from the formulation in Table 4 without any ionic components added. Comparative Example 6 lenses were made from the formulation in Table 4 with 3% MAA as the ionic component. Comparative Examples 7 and 8 are made from the formulation in Table 6. The procedure for making the lenses of Comparative Examples 7 and 8 are described below.

TABLE 5

| Ex# | Ionic Species (mol %) | Ionic Species (mol/gm) | Lysozyme Uptake (μg/lens) | PQ1 Uptake (%) | [H2O] (%) |
|---|---|---|---|---|---|
| CE5 | None | 0 | 5.5 ± 0.55 | 8 ± 3 | 43 ± 0.1 |
| CE 6 | 3% MAA | 1.33 × 10⁻⁴ | 143 ± 9 | 82 ± 1 | 52 ± 0.2 |
| 13 | 3% ACA1 | 1.35 × 10⁻⁴ | 142 ± 10 | 9 ± 1 | 53 ± 0.2 |
| 14 | 3% ACA2 | 1.35 × 10⁻⁴ | 98 ± 29 | 7 ± 1 | 54 ± 0.1 |
| CE7 | None | 0 | 5.2 ± 0.2 | 6 ± 3 | 37 ± 0.2 |
| CE8 | 1.5% MAA | 6.5 × 10⁻⁵ | 116 ± 3 | 100 ± 0 | 47 ± 0.1 |

Comparative Example 6 is an ionic mixed methacrylate (MAA)/methacrylamide (SA2, bisHEAA, DMA, MBA) system. The addition of 3 mol % MAA greatly improved lysozyme uptake compared to Comparative Example 5, which is the same formulation without any ionic component. However, Comparative Example 6 displayed dramatically increased PQ1 uptake. Examples 13 and 14 contain ACA1 and ACA2 as the ionic component, both of which are acrylamides. They also display significantly improved lysozyme uptake, but show no increase in PQ1 uptake compared to Comparative Example 5. The lenses of the invention are formed from reaction mixtures comprising the same reactive functionality (in Examples 13-14, acrylamide). This provides a statistical copolymer with the anionic charge evenly distributed throughout the lens. It is believed that the desirable combination of properties results from this consistent distribution of charge throughout the lenses of the invention.

The formulations of Comparative Examples 7-8 contain monomers having methacrylate functionality (mPDMS, HOmPDMS, HEMA) and methacrylamide functionality (DMA). Thus, Comparative Example 8, displays very high PQ-1 uptake (100%).

Comparative Examples 7 and 8

Comparative Example lenses were formed by mixing the components, in the amounts listed in Table 6 with D3O (23% D3O:77% components). Comparative Example 8 used the same formulation, but with 1.5 mol % MAA added to the formulation.

TABLE 6

| Compound | Wt % | Mole % |
| --- | --- | --- |
| mPDMS | 27.53 | 7.8 |
| HOmPDMS | 36.07 | 16.6 |
| TEGDMA | 1.33 | 1.3 |
| DMA | 21.31 | 60.8 |
| HEMA | 5.33 | 11.6 |
| PVP K-90 | 6.22 | 1.83 |
| Irgacure 819 | 0.43 | 0.29 |
| Norbloc 7966 | 1.78 | 1.6 |
| Blue HEMA | 0.02 | 0.007 |

The formulations were dosed in to molds (Zeonor FC/polypropylene BC) and cured for 5 minutes, at about 55° C., about 2.25 mW/cm$^2$ intensity, and about 0.2% $O_2$. The lenses were released and extracted in 70/30 IPA/DI and finally hydrated in standard packing solution. The lenses were sterilized at 121° C. for 20 minutes.

The lysozyme and PQ1 uptake were measured and are shown in Table 5, above.

Examples 15-20

A base reactive mixture having the components listed in Table 7, below was made by mixing the components in the amounts listed with t-amyl alcohol (55 wt % components:45 wt % t-amyl alcohol).

TABLE 7

| Component | Wt % |
| --- | --- |
| DMA | 30.90 |
| Norbloc | 2.00 |
| Irgacure 819 | 0.125 |
| MBA | 1.300 |
| SA2 | 55.65 |
| PVP K90 | 7.00 |
| bis-HEAA | 3.02 |

Formulations were made adding ACA1 as the ionic component in the amounts listed in Table 8, below. Comparative Example 9 was formed from the formulation in Table 7, with no ACA1 added. The formulations were stirred on a jar roller for 2 hours, and then filtered.

Each reactive mixture was degassed, dosed into molds (Zeonor TuffTec FC/polypropylene BC) and cured for 5 minutes, at about 60° C., about 1.5 mW/cm$^2$ intensity, and about 0.2% $O_2$. The molds were separated by hand. The lenses were released and extracted in 70/30 IPA/DI and finally hydrated in standard packing solution. The lenses were sterilized at 121° C. for 20 minutes. The sterilized lenses were tested for water content, lysozyme and PQ1 uptake. The results are shown in Table 8, below.

TABLE 8

| Ex# | [ACA1] (mol %) | [ACA1] (mol/gm) | Lysozyme Uptake (µg/lens) | PQ1 Uptake (%) | [H$_2$O] (%) |
| --- | --- | --- | --- | --- | --- |
| CE9 | 0 | 0 | 5 ± 1 | 2 ± 3 | 40 ± 0.1 |
| 15 | 0.25 | 1.2 × 10$^{-5}$ | 86 ± 11 | 4 ± 2 | 43 ± 0.3 |
| 16 | 0.5 | 2.4 × 10$^{-5}$ | 150 ± 5 | 6 ± 1 | 43 ± 0.2 |
| 17 | 1.0 | 4.7 × 10$^{-5}$ | 145 ± 7 | 5 ± 4 | 46 ± 0.2 |
| 18 | 1.5 | 7.0 × 10$^{-5}$ | 152 ± 7 | 6 ± 1 | 49 ± 0.1 |
| 19 | 3.0 | 1.4 × 10$^{-4}$ | 151 ± 7 | 5 ± 4 | 53 ± 0.2 |
| 20 | 6.0 | 2.8 × 10$^{-4}$ | 163 ± 5 | 61 ± 2 | 62 ± 0.1 |

This series shows that a wide range (0.25 to 3 mol %) anionic component can be used to achieve the desired increase in lysozyme uptake without increasing PQ1 uptake or undesirably increasing water content. Example 20 shows undesirable PQ1 uptake. It is believed that even though the charges are evenly distributed throughout the lens copolymer, the concentration is high enough to attract significant quantities of PQ1. These lenses would be undesirable for reusable lenses, but could be suitable for daily disposable lenses which are not cleaned and are generally not contacted with multipurpose solutions.

Comparative Examples 10-13

A base reactive mixture having the components listed in Table 6, above was made by mixing the components in the amounts listed with D3O (77 wt % components:23 wt % D3O).

Formulations were made adding MAA as the ionic component in the amounts listed in Table 9, below. The formulations were stirred on a jar roller for 2 hours, and then filtered.

Each reactive mixture was degassed, dosed into molds (Zeonor TuffTec FC/polypropylene BC) and cured for 5 minutes, at about 60° C., about 1.5 mW/cm$^2$ intensity, and about 0.4% $O_2$. The molds were separated by hand. The lenses were released and extracted in 70/30 IPA/DI and finally hydrated in standard packing solution. The lenses were sterilized at 121° C. for 20 minutes. The sterilized lenses were tested for water content, lysozyme and PQ1 uptake. The results are shown in Table 9, below.

TABLE 9

| Ex# | [MAA] (mol %) | [MAA] (mol/gm) | Lysozyme Uptake (µg/lens) | PQ1 Uptake (%) | [H2O] (%) |
| --- | --- | --- | --- | --- | --- |
| CE10 | 0 | 0 | 5 ± 0.2 | 0.7 | 38 ± 0.2 |
| CE11 | 0.5 | 2.2 × 10$^{-5}$ | 29 ± 3 | 5 | 42 ± 0.2 |
| CE12 | 0.8 | 3.6 × 10$^{-5}$ | 42 ± 3 | 36 | 45 ± 0.1 |
| CE13 | 1.1 | 5.1 × 10$^{-5}$ | 67 ± 3 | 100 | 46 ± 0.0 |

The formulation in Table 9 contains both methacrylate components (HO-mPDMS, HEMA and mPDMS) as well as acrylamide components (DMA). Comparative Examples 10-13 show that such systems cannot provide the desired balance of lysozyme uptake greater than 50 µg/lens and PQ1 uptake of less than about 10%.

Examples 20-24

A base reactive mixture having the components listed in Table 10, below was made by mixing the components in the amounts listed with t-amyl alcohol (65 wt % components:35 wt % t-amyl alcohol).

TABLE 10

| Component | Wt % |
| --- | --- |
| DMA | 39.41 |
| Norbloc 796 | 62.00 |
| Irgacure 819 | 0.125 |
| MBA | 1.00 |
| SA2 | 49.51 |
| PVP K90 | 7.95 |

Formulations were made adding AMPS as the ionic component in the amounts listed in Table 11, below. The formulations were stirred on a jar roller for 2 hours, and then filtered. Each reactive mixture was degassed, dosed into molds (Zeonor TuffTec FC/polypropylene BC) and cured for 5 minutes, at about 60° C., about 1.9 mW/cm² intensity, and about 0.2% $O_2$. The molds were separated by hand. The lenses were released and extracted in 70/30 IPA/DI and finally hydrated in standard packing solution. The lenses were sterilized at 121° C. for 20 minutes. The sterilized lenses were tested for water content, lysozyme and PQ1 uptake. The results are shown in Table 11, below.

TABLE 11

| Ex# | [AMPS] (mol %) | [AMPS] (mol/gm) | Lysozyme Uptake (µg/per lens) | PQ1 Uptake (%) | [H₂O] (wt %) |
| --- | --- | --- | --- | --- | --- |
| 20 | 0.25 | 1.2 × 10⁻⁵ | 87 ± 4 | 4 ± 1 | 50 ± 0.1 |
| 21 | 0.5 | 2.5 × 10⁻⁵ | 145 ± 2 | 3 ± 1 | 53 ± 0.2 |
| 22 | 1.0 | 5.1 × 10⁻⁵ | 143 ± 4 | 1 ± 1 | 58 ± 0.1 |
| 23 | 1.4 | 7.0 × 10⁻⁵ | 166 ± 11 | 6 ± 3 | 69 ± 0.2 |
| 24 | 3.0 | 1.4 × 10⁻⁴ | Not tested | 16 ± 3 | 72 ± 0.1 |

This series shows that a wide range (0.25 to 3 mol %) anionic component can be used to achieve the desired increase in lysozyme uptake without increasing PQ1 uptake. Example 24 shows undesirable PQ1 uptake. It is believed that even though the charges are evenly distributed throughout the lens copolymer, the concentration is high enough to attract significant quantities of PQ1. These lenses would be undesirable for reusable lenses, but could be suitable for daily disposable lenses which are not cleaned and are generally not contacted with multipurpose solutions. The lenses of Example 24 were also fragile and displayed an undesirably high water content. Thus, this Example series shows that concentrations of AMPS between about 0.2 and about 1.5 mol % provide a desirable combination of lysozyme and PQ1 uptake, and water content.

Synthesis 4: VINAL 4.82 g vinyl chloroformate (Aldrich) was added to 8.19 g β-alanine (Aldrich) dissolved in 74 ml acetonitrile. The mixture was refluxed under nitrogen and with stirring for 2 hours. It was cooled to room temperature for 2 hours, then filtered. The solvent was removed under reduced pressure.

This crude product was dissolved in 30 ml water and washed three times with ethyl acetate. The combined ethyl acetate fractions were washed with 50 ml water. The solvent was stripped off to yield 4.51 g VINAL as an off-white solid.

Synthesis 5: N-dodecyl-O-vinylcarbamate (DVC)

3.0 g dodecylamine (Aldrich), 4.0 g $Na_2CO_3$ and 30 ml $CH_2Cl_2$ were placed into a 100 ml round bottomed flask with a stir bar and thermocouple thermometer, and under nitrogen. The flask was placed into a room temperature water bath. 1.9 g vinylchloroformate (Aldrich) was added via a side armed addition funnel. There was a modest exotherm. The mixture was stirred for about 4 hours at room temperature, filtered and washed once with 1.0N HCl and twice with water. It was dried over $Na_2SO_4$ and the solvent was stripped off to yield the crude product as a mushy solid.

The crude product was dissolved in a minimal amount of methanol, and precipitated with water. The solvent was removed and the crystals were dried under vacuum to yield 2.2 g product.

Preparation 9: PVP-Co-VINAL (2 wt %)

19.6 g N-vinylpyrrolidone (ACROS, 98%), 0.40 g VINAL and 10 µl 2-hydroxy-2-methylpropiophenone (Aldrich) were combined to form a clear blend. The solution was placed into two 14 mm diameter polypropylene tubes. These tubes were irradiated with UV light from 4 Philips TL 20 W/09N fluorescent bulbs for 4 hours in a nitrogen environment. The solid polymer was removed from the tubes and stirred in 150 ml tetrahydrofuran to dissolve. This solution was poured into 700 ml diethyl ether with stirring to precipitate the polymer. The solid was recovered by filtration, redissolved in THF, and reprecipitated with diethyl ether. It was recovered by filtration and dried for 48 hours under vacuum to yield polymer as a soft white solid.

Preparation 10—PVP-Co-VINAL(2 wt %)-Co-DVC(2 wt %)

The procedure of Preparation 9 was used to form copolymer from 4.8 g N-vinylpyrrolidone, 0.1 g VINAL, 0.1 g DVC and 6 µl 2-hydroxy-2-methylpropiophenone.

Preparation 11—PVP

The procedure of Preparation 9 was used to form PVP homopolymer from 10 g N-vinylpyrrolidone and 6 µl 2-hydroxy-2-methylpropiophenone.

Comparative Examples 13-15

Solutions having a concentration of 1 wt % were formed by adding 1 g of each of the polymers made in Preparations 9-11 in 100 g borate buffered saline solution (pH 7.4) and mixing for 2 hours at 60° C. 3 ml of each solution was placed into each of several vials. One senofilcon A contact lens (ACUVUE OASYS™ BRAND CONTACT LENSES with HYDRACLEAR™ Plus) was placed into each vial. The vials were sealed and autoclaved at 121° C. for 30 minutes. The lenses were rinsed in fresh borate buffered saline and tested for contact angle using the sessile drop method. The results are shown in Table 11.

TABLE 11

|  | CE14 | CE15 | CE16 |
| --- | --- | --- | --- |
| Polymer | PVP-VINAL (2%) | PVP-VINAL(2%)-DVC(2%) | PVP |
| Contact angle | 37 ± 6° C. | 38 ± 10° C. | 60 ± 10° C. |
| Lysozyme (µg/lens) | 5.75 ± 0.2 | 5.46 ± 0.12 | NM |

Desirable decreases in contact angle were achieved however, the lysozyme uptake was not significantly increased. Comparing Comparative Examples 14 and Example 19, which contained 2-4 mol % anionic monomer to Examples 2-4, it is believed that increasing the concentration of the anionic monomers in polymers used in Comparative Examples 14 and 15 to at least about 20 mol % and in some embodiments at least about 30 mol % or greater, will provide the desired lysozyme uptake.

We claim:

1. A silicone hydrogel formed from a reactive mixture comprising
   major polymerizable components comprising at least one reactive silicone-containing component, at least one reactive ionic monomer, crosslinker, and optional reactive hydrophilic components; and
   minor components that are optionally polymerizable comprising at least one pharmaceutical compound or nutriceutical compound, and optional additional minor polymerizable components selected from the group consisting of visibility tint and dyes, UV absorbers, photochromic compounds, and mixtures thereof;
   wherein said major polymerizable components comprise a single reactive functionality; and wherein any polymerizable components in the reaction mixture which have a reactive functionality different than said single reactive functionality are present in a concentration less than 0.5 mol %.

2. The silicone hydrogel of claim 1 wherein said single reactive functionality is selected from the group consisting of acrylate, methacrylate, acrylamide, methacrylamide, vinyl and styryl.

3. The silicone hydrogel of claim 1 wherein said single reactive functionality is selected from the group consisting of acrylamide, methacrylamide and vinyl.

4. The silicone hydrogel of claim 1 wherein said single reactive functionality is methacrylamide and said reactive ionic monomer comprises at least one acrylamido sulphonic acid or acrylamido sulphonic acid salt.

5. The silicone hydrogel of claim 4 wherein said acrylamido sulphonic acid comprises an alkylene group comprising 2 to 4 carbon atoms.

6. The silicone hydrogel of claim 4 wherein said acrylamido sulphonic acid salt comprises 2-acrylamido-2-methylpropane sulfonic acid salt.

7. The silicone hydrogel of claim 1 wherein said at least one pharmaceutical or nutraceutical component is cationic.

8. The silicone hydrogel of claim 1 wherein said at least one pharmaceutical or neutraceutical component is selected from the group consisting of
   atropine, pirenzepine, doxycycline, brimonidine, brinzolamide, dorzolamide, betaxolol, apraclonidine, ccr2 antagonist, olopatadine, alcaftadine, betaxolol, bupivacaine, carbachol, carteolol, chlortetracycline, cyclopentolate, dibutoline, dipivefrin, ephedrine, erythromycin, gentamycin, gramicidin, homatropine ketotifen, levobunolol, levocastine, lidocaine, lignocaine, lomefloxacin, mepivacaine, naphazoline, neomycin, ofloxacin, oxybuprocaine, pheniramine, physostigmine, pilocarpine, polymyxin B, proparacaine, pyrilamine, tetracaine, tetracycline, tetrahydozoline, timolol, tropicamide, vidarabine, pharmaceutically acceptable salts thereof and combinations thereof.

9. The silicone hydrogel of claim 1 wherein said at least one pharmaceutical or neutraceutical component is selected from the group consisting of atropine, pirenzepine, doxycycline, brimonidine, brinzolamide, dorzolamide, betaxolol, apraclonidine, ccr2 antagonist, olopatadine, alcaftadine, betaxolol, bupivacaine, carbachol, carteolol, chlortetracycline, cyclopentolate, dibutoline, dipivefrin, erythromycin, gentamycin, gramicidin, homatropine ketotifen, levobunolol, levocastine, lidocaine, lignocaine, lomefloxacin, mepivacaine, naphazoline, ofloxacin, pheniramine, physostigmine, pilocarpine, polymyxin B, proparacaine, pyrilamine, tetracaine, tetracycline, tetrahydozoline, timolol, tropicamide, pharmaceutically acceptable salts thereof and combinations thereof.

10. The silicone hydrogel of claim 1 wherein said at least one pharmaceutical or nutraceutical component is selected from the group consisting of atropine, ketotifen, olopatadine, alcaftadine, levocastine, pirenzepine, doxycycline, brimonidine, brinzolamide, dorzolamide, betaxolol, apraclonidine, ccr2 antagonist, olopatadine, pharmaceutically acceptable salts thereof and combinations thereof.

11. A contact lens comprising the silicone hydrogel of claim 1, wherein said at least one pharmaceutical or nutraceutical component in a symptom mitigating effective amount.

12. The contact lens of claim 11 wherein said symptom mitigating effective amount is between about 5 μg and less than 200 μg.

13. The contact lens of claim 11 wherein said symptom mitigating effective amount is between about 9 μg and about 100 μg.

14. The contact lens of claim 11 wherein said symptom mitigating effective amount alleviates symptoms for between about 5 minutes, and about 12 hours from insertion of said contact lens on a human's eye.

15. The contact lens of claim 11 wherein said contact lens comprises a modulus which increases less than 30% after three autoclave cycles.

16. The contact lens of claim 11 further comprising a lysozyme uptake of at least 70 μg/lens.

17. The contact lens of claim 11 further comprising a lysozyme uptake of at least 100 μg/lens.

18. The contact lens of claim 11 further comprising a water content of between about 20% and about 70%.

19. The contact lens of claim 11 further comprising a water content of between about 25% and about 65%.

20. The silicone hydrogel of claim 1 wherein said single reactive functionality is selected from (meth)acrylamides.

21. The silicone hydrogel of claim 1 wherein said single reactive functionality is selected from (meth)acrylates.

22. The silicone hydrogel of claim 1 wherein said single reactive functionality is selected from vinyls.

23. The silicone hydrogel of claim 20 wherein said reactive ionic monomer is selected from the group consisting of 3-acrylamidopropionic acid, 4-acrylamidobutanoic acid, 5-acrylamidopentanoic acid, sodium-2-(acrylamido)-2-methylpropane sulphonate, 2-acrylamido-2-methylpropane sulfonic acid and combinations thereof.

24. The silicone hydrogel of claim 21 wherein said reactive ionic monomer is selected from the group consisting of (meth)acrylic acid, acrylic acid, 3-sulphopropyl (meth)acrylate potassium salt, 3-sulphopropyl (meth)acrylate sodium salt, sulphoethyl methacrylate, and mixtures thereof.

25. The silicone hydrogel of claim 21 wherein said reactive ionic monomer comprises (meth)acrylic acid.

26. The silicone hydrogel of claim 22 wherein said reactive ionic monomer is selected from the group consisting of N-vinyloxycarbonyl-α-alanine, N-vinyloxycarbonyl-β-alanine, 2-vinyl-4,4-dimethyl-2-oxazolin-5-one, vinyl sulphonate sodium salt, vinyl sulphonate salt, and mixtures thereof.

* * * * *